ions of the page.

United States Patent [19]

Roques et al.

[11] Patent Number: 4,618,708

[45] Date of Patent: Oct. 21, 1986

[54] AMINO ACID DERIVATIVE

[76] Inventors: Bernard Roques, 12 Rue E. Delacroix, 94410 St. Maurice; Jean-Charles Schwartz, 9, Villa Seurat, 75014 Paris; Jeanne-Marie Lecomte, 30 Rue des Francs-Bourgeois, 75003 Paris, all of France

[21] Appl. No.: 715,764

[22] Filed: Mar. 25, 1985

Related U.S. Application Data

[63] Continuation of Ser. No. 449,687, Dec. 14, 1982, abandoned.

[30] Foreign Application Priority Data

Dec. 16, 1981 [FR] France ............................ 81 23488

[51] Int. Cl.$^4$ .................. C07C 101/24; C07C 103/52
[52] U.S. Cl. ............................ 562/448; 260/502.4 R; 260/507 R; 260/500 SH; 560/13; 560/39; 560/41; 560/312; 562/430; 562/450; 548/201; 548/533; 564/152; 564/154; 546/233; 514/563; 514/542; 514/7; 514/2

[58] Field of Search ................ 562/448; 260/112.5 R, 260/112.5 E

[56] References Cited

U.S. PATENT DOCUMENTS 4,146,641  3/1979  Ondetti et al. .................. 562/448 X

*Primary Examiner*—Bernard Helfin
*Attorney, Agent, or Firm*—Young & Thompson

[57] ABSTRACT

Derivatives having the general formula:

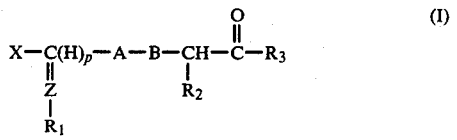

in which the various radicals A,B,X,$R_1$, $R_2$, $R_3$ and n have indicated definitions. These compounds have in particular enkephalinase-inhibiting, antalgic, antidepressive, antidiarrhea and hypotensive activities.

1 Claim, No Drawings

AMINO ACID DERIVATIVE

This application is a continuation of application Ser. No. 449,687, filed 12/14/82 and now abandoned.

DESCRIPTION

The present invention relates to new amino acid derivatives, to their process of preparation and to their therapeutic application.

The derivatives according to the invention are inhibitors of enzymes, and in particular enkephalinase which is an enkephalin-degrading enzyme (B. Malfroy et al, Nature 276, 523 (1978); A. Guyon et al, Life Sciences 25, 1605 (1979)) and peptidases, such as aminopeptidases involved in the metabolism of opioid peptides (Hambrook et al, Nature (1976) 262, 782; Pert et al, (1976) Science 194, 330–332; Guyon et al, Biochem. Biophys. Res. Commun. (1979) 88, 919–926.

The compounds capable of inhibiting enkephalinase may thus prolong the effects of endogenic enkephalins or potentitate the action of synthetic analogs administered in an exogenous manner. Thus these compounds may replace morphinic agents in all their properties without having the serious drawbacks of the latter, particularly in respect of habit-forming and dependence phenomena.

Dipeptide derivatives having an enkephalinase-inhibiting action are already known from the patent application FR No. 80/05 601.

An object of the present invention is to provide new dipeptide derivatives or analogs having in particular this action.

These derivatives according to the invention have the following general formula:

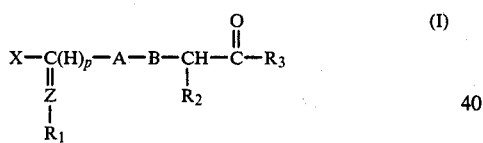

in which
- A is a group selected from carbonyl, amino and —CH$_2$—CO— when B=NH;
- B is selected from a carbonyl group; an amino group; an amino group substituted with a C$_{1-4}$ alkyl group, a substituted amino group whose third valence forms with the R$_2$ group an alkylenic chain having 2 to 4 carbon atoms and optionally containing a sulfur atom or a nitrogen atom and/or optionally substituted with a hydroxy or C$_{1-4}$ alkoxy group;
- R$_1$ is an hydrogen atom; a straight or branched-chain C$_{1-6}$ alkyl group optionally mono- or polysubstituted with a halogen atom; a cyclohexyl group; a phenyl or naphthyl group optionally mono- or polysubstitued with a halogen atom, a trifluoromethyl or hydroxy group; a thienyl group; a thiazolyl group; a furyl group; an indolyl group; an imidazolyl group;
- Z is —(CH$_2$)$_n$— or =(CH)—;
- n is 0,1 or 2; p is 0 when Z is =CH— and p is 1 in the other cases;
- R$_2$ is a hydrogen atom; a straight or branched-chain C$_{1-6}$ alkyl group; a C$_{1-4}$ alkyl group substituted with a residue α or β thienyl, α or β furyl, α or β thiazolyl, α or β indolyl, α or β imidazolyl, α or β benzothienyl, α or β benzimidazolyl, naphthyl or a phenyl group optionally mono- or polysubstituted with a halogen atom; a hydroxyalkyl group; an alkoxyalkyl group optionally substituted on the alkoxy moiety with a phenyl, benzhydryl or pyridyl group optionally N-substituted with a phenylalkyl group whose phenyl nucleus is itself optionally substituted with one or more halogen atoms; a phenoxyalkyl group; a mercapto alkyl group optionally substituted on the sulfur with a straight or branched-chain alkyl group, phenyl or benzyl group;
- R$_3$ is a hydroxy group; a straight or branched-chain C$_{1-8}$ alkoxy group optionally mono- or polyhalosubstituted with a halogen atom, a hydroxy C$_{3-6}$ cycloalkyl group, amino or aminoxide group, the latter two radicals being optionally mono- or disubstituted with a C$_{1-4}$ alkyl group, a C$_{1-8}$ alkoxy group substituted with a thienyl, thiazolyl, pyrrolidinyl, piperidyl, piperazinyl, or morpholinyl group, these latter heterocyclic groups being optionally substituted with a hydroxy or hydroxy C$_{1-4}$ alkyl group; a phenoxy or phenyl C$_{1-4}$ alkoxy group whose phenyl nucleus is optionally mono- or poly-substituted with a halogen atom, a hydroxy, C$_{1-4}$ alcoxy or trihalogenomethyl group; an amino group; an amino group mono- or disubstituted with a straight or branched-chain C$_{1-18}$ alkyl group optionally mono- or polysubstituted with a halogen atom, a hydroxy, mercapto, C$_{1-4}$ alkylthio, C$_{1-4}$ alkylsulfinyl radical; an amino group optionally mono- or disubstituted with a phenyl or phenyl C$_{1-4}$ alkyl group, the latter two radicals being optionally mono- or polysubstituted on the phenyl nucleus with a halogen atom; a group of the formula

in which R$_4$ and R$_5$ form with the nitrogen atom to which they are attached a heterocyclic nucleus having 5 or 6 members which may optionally comprise another heteroatom selected from N, O, S and this heterocycle being optionally mono- or disubstituted with a hydroxy, hydroxy(C$_{1-4}$)alkyl, C$_{1-4}$ alkoxy group, C$_{1-4}$ alkoxy group substituted with a phenyl radical optionally substituted with a C$_{1-4}$ alkyl radical, hydroxy, C$_{1-4}$ alkoxy radical or a halogen atom, the heterocycle also optionally comprising as a mono- or disubstituent a carboxy, C$_{1-4}$alkoxy carbonyl, C$_{1-4}$ alkoxy carbonyl group whose alkoxy group is substituted with a phenyl group optionally substituted with a C$_{1-4}$ alkyl, hydroxy, C$_{1-4}$ alcoxy group or a halogen atom;
- X is a phosphono group; a substituted phosphonyl group of formula —PO(OR)$_2$ in which R is a C$_{1-4}$ alkyl group or an aralkyl group; a sulfo group; an amino group; a mono-substituted amino group of formula NHR' in which R' is an alkyl, cycloalkyl, phenyl, mono- or polyhalophenyl, phenyl C$_{1-4}$ alkyl, mono- or polyhalophenyl C$_{1-4}$ alkyl, hydroxy, C$_{1-6}$ alkoxy, aralkoxy, mono- or polyhaloaralkoxy whose alkoxy moiety has from 1 to 4 carbon atoms, phosphono group, substituted phosphonyl group of formula —PO(OR)$_2$ in which R is as defined above or sulfo; a disubstituted amino group of formula

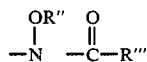

in which R" is a hydrogen atom, a $C_{1-6}$ alkyl, a $C_{1-4}$ alkoxy carbonyl, aroyl, $C_{1-4}$ aralkyl group optionally mono- or polysubstituted on the aryl nucleus with a radical selected from a halogen atom, a hydroxy, amino, nitro or trifluoromethyl group, R''' is a hydrogen atom, an alkyl group optionally mono- or polysubstituted with a halogen atom or a trifluoromethyl group, a $C_{1-4}$ aralkyl group optionally mono- or polysubstituted on the aryl nucleus with a radical selected from a halogen atom, a hydroxy, amino, nitro or trifluoromethyl group; a mono- or disubstituted carbamoyl group of formula

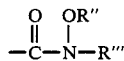

in which R" and R''' are as defined above; a $C_{1-4}$ alkyl group mono- or polysubstituted with a phosphono group, a disubstituted phosphono group of formula $-PO(OR)_2$ in which R is as defined above, or a sulfo group; an aminoalkyl group; a monosubstituted aminoalkyl group of formula $-(CH_2)_m-NHR'$ in which R' is as defined above, and m is an integer of 1 to 4; a disubstituted aminoalkyl group of formula

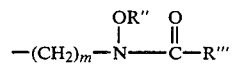

in which R", R''' and m are as defined above, a mono- or disbustituted carbamoyl alkyl group of formula

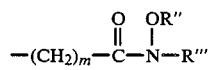

in which R", R''' and m are as defined above; provided that there are not simultaneously $R_1=R_2=X=H$, $R_3=OH$, $n=O$, $A=CO$ and $B=NH$;
and the addition salts thereof with pharmaceutically acceptable acids or bases.

Among the compounds of the formula I defined above, a preferred class of the compounds comprises the derivatives in which:

A is a carbonyl, amino, or $-CH_2-CO-$ group when B is NH;

B is a carbonyl or amino group or a substituted amino group whose third valence forms with $R_2$ a $C_{2-4}$ alkylene radical optionally containing another heteroatom;

$R_1$ is a hydrogen atom; $C_{1-4}$ alkyl group; a phenyl group, optionally mono- or polysubstituted with a halogen atom; an indolyl group;

$R_2$ is a hydrogen atom; a straight or branched alkyl group optionally substituted with an indolyl group;

Z and p are as defined above;

n is 0 or 1;

$R_3$ is a hydroxy group; $C_{1-4}$ alkoxy optionally mono- or polysubstituted with a halogen atom; a $C_{1-4}$ alkoxy group substituted with a dialkylamino group in which the alkyl groups contain 1–4 carbon atoms, dialkylaminoxide, piperidino or hydroxy piperidino group; a phenyl $C_{1-4}$ alkoxy group whose phenyl group is optionally substituted with a halogen atom; an amino group; $C_{1-6}$ alkyl amino whose alkyl group is optionally mono- or polysubstituted with a halogen atom; a hydroxy, mercapto, $C_{1-4}$ alkylthio, $C_{1-4}$ alkylsulfinyl radical; phenyl $C_{1-4}$ alkyl amino whose phenyl group is optionally mono- or polysubstituted with a halogen atom; pyrrolidino mono- or disbustituted with a hydroxy, carboxy, $C_{1-4}$ alkoxycarbonyl or benzyloxy radical;

X is a phosphono group; a phosphono group substituted with at least a benzyl radical; a sulfo group; an amino group mono- or disubstituted with a radical selected from a hydroxy, benzyloxy, phosphono group, or a phosphono group mono- or disubstituted with a benzyl, sulfo, formyl, benzylcarbonyl or mono- or polyhalo $C_{1-4}$ alkyl carbonyl group; a carbamoyl group mono- or disubstituted with a radical selected from a hydroxy group or a benzyloxy group whose phenyl group is optionally mono- or polysubstitued with a halogen atom, or mono- or polyhalobenzyl; an alkyl group optionally mono- or polysubstituted with a radical selected from a phosphono group or a phosphono group disubstituted with a benzyl, sulfo group, an amino alkyl group mono- or disubstituted on the nitrogen atom with a radical selected from a $C_{1-4}$ alkyl, hydroxy, benzyloxy, phosphono, sulfo, formyl, acetyl, mono- or polyhalobenzylcarbonyl, mono- or polyhalo $C_{1-4}$ alkyl carbonyl group; a $C_{1-4}$ alkyl group substituted with a carbamoyl radical mono- or disubstituted with an alkyl, hydroxy, benzyloxy radical whose phenyl group is optionally mono- or polysubstituted with a halogen atom, mono- or polyhalobenzyl, acetyl or benzoyl.

As a halogen atom, preference is particularly given to fluor.

Unless otherwise indicated, the alkyl groups have preferably 1 to 6 carbon atoms and in particular 1 to 4 carbon atoms.

As an aryl group, there is envisaged any mono- or polycyclic aromatic nucleus optionally containing a heteroatom such as nitrogen, sulfur or oxygen, and the phenyl group is particularly preferred.

Specific compounds contemplated by the invention are the following derivatives (in the following formulae $\phi$=the phenyl group):

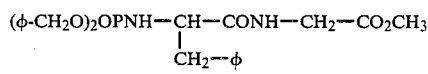   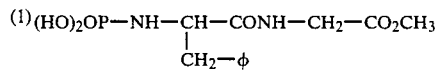

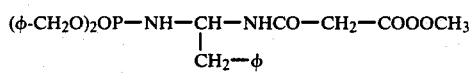(3)
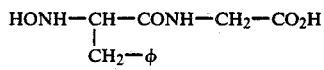(5)
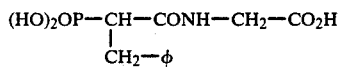(7)
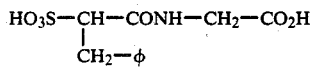(9)
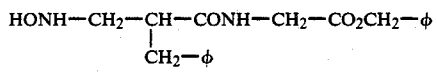(11)
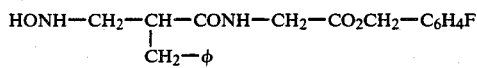(13)
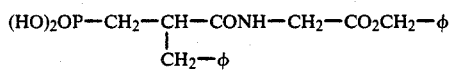(15)
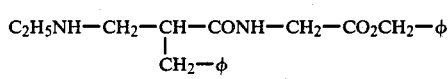(17)
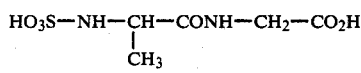(19)
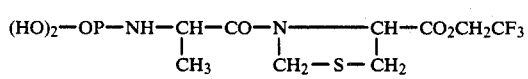(21)
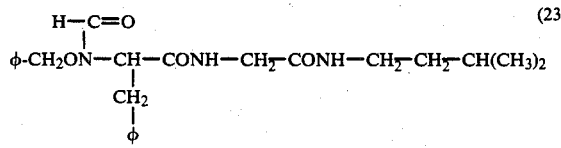(23)
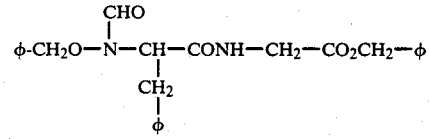(25)
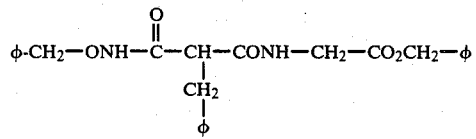(27)
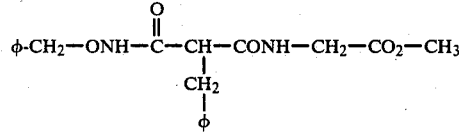(29)
-continued
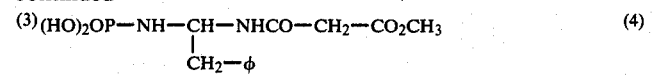(4)
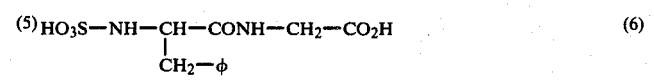(6)
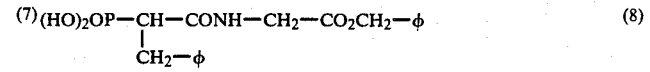(8)
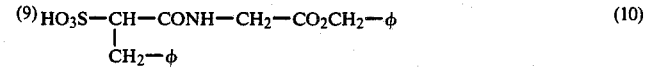(10)
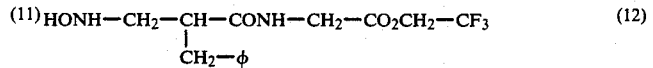(12)
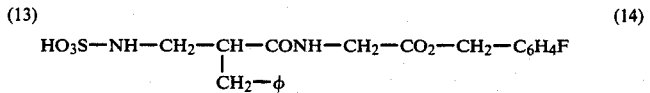(14)
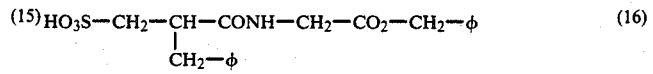(16)
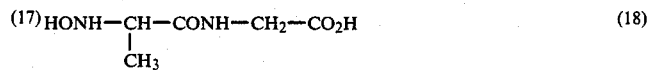(18)
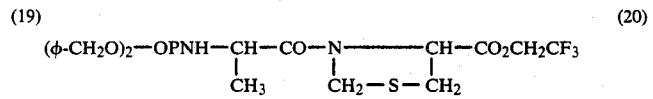(20)
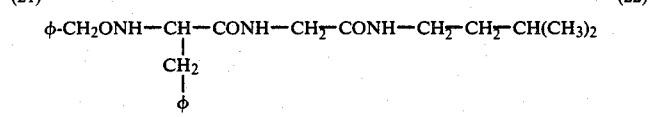(22)
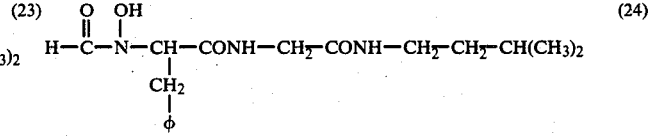(24)
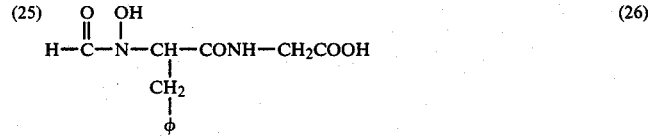(26)
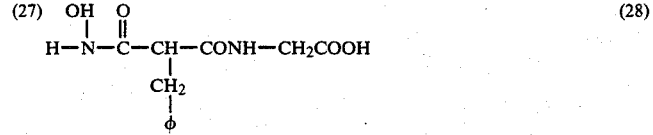(28)
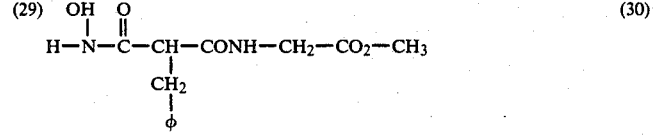(30)

-continued

(31) φ-CH₂—ONH—C(=O)—CH(CH₂φ)—CONH—CH₂—CONH—CH₂—φ

(32) HO-HN—C(=O)—CH(CH₂φ)—CONH—CH₂—CONH—CH₂—φ

(33) φ-CH₂—ONH—C(=O)—CH(CH₂φ)—CONH—CH₂—CONH—CH₂—CH₂—CH(CH₃)₂

(34) HO-HN—C(=O)—CH(CH₂φ)—CONH—CH₂—CONH—CH₂—CH₂—CH(CH₃)₂

(35) φ-CH₂O—N(CHO)—CH₂—CH(CH₂φ)—CONH—CH₂—CONH—CH₂—CH₂—CH(CH₃)₂

(36) H—C(=O)—N(OH)—CH₂—CH(CH₂φ)—CONH—CH₂—CONH—CH₂—CH₂—CH(CH₃)₂

(37) φ-CH₂O—N(CHO)—CH₂—CH(CH₂—φ)—CONH—CH₂—COOCH₂—φ

(38) H—C(=O)—N(OH)—CH₂—CH(CH₂—φ)—CONH—CH₂—COOH

(39) φ-CH₂O—N(CHO)—CH₂—CH(CH₂—φ)—CONH—CH₂—CO₂—CH₃

(40) H—C(=O)—N(OH)—CH₂—CH(CH₂—φ)—CONH—CH₂—CO₂—CH₃

(41) φ-CH₂O—N(COCH₃)—CH₂—CH(CH₂φ)—CONH—CH₂—CO₂—CH₂—φ

(42) CH₃CO—N(OH)—CH₂—CH(CH₂φ)—CONH—CH₂—CO₂H

(43) φ-CH₂O—N(COCH₃)—CH₂—CH(CH₂—φ)—CONH—CH₂—CONH—CH₂—φ

(44) CH₃CO—N(OH)—CH₂—CH(CH₂—φ)—CONH—CH₂—CONH—CH₂—φ

(45) φ-CH₂—ONH—C(=O)—CH₂—CH(CH₂φ)—CONH—CH₂—CO₂tbu

(46) φ-CH₂—ONH—C(=O)—CH₂—CH(CH₂φ)—CONH—CH₂—COOH

(47) HONH—C(=O)—CH₂—CH(CH₂φ)—CONH—CH₂—CO₂H

(48) φ-CH₂—ONH—CO—CH₂—CH(CH₂—φ)—CONH—CH₂—CONH—CH₂—φ

(49) HONH—CO—CH₂—CH(CH₂—φ)—CONH—CH₂—CONH—CH₂—

(50) φ-CH₂—O—N(C(=O)—CH₂—φ)—CH(CH₂—φ)—CONH—CH₂—CO₂—CH₂—φ

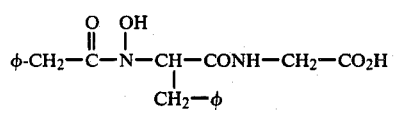(51)
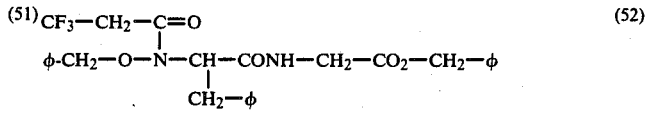(52)
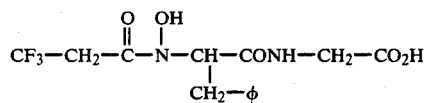(53)
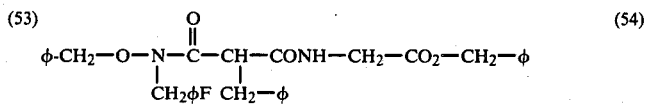(54)
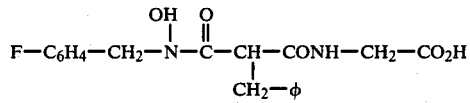(55)
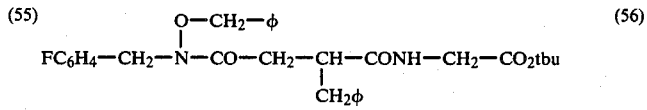(56)
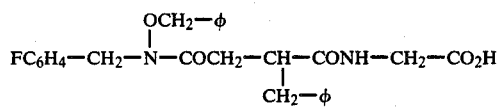(57)
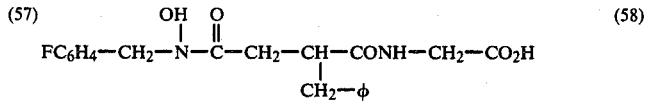(58)
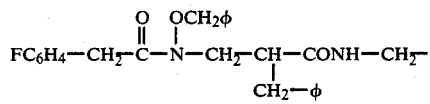(59)
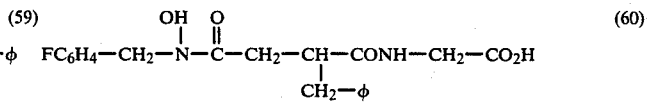(60)
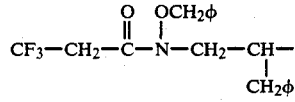(61)
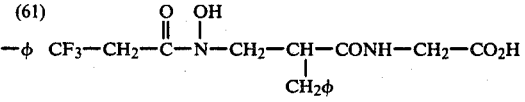(62)
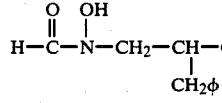(63)
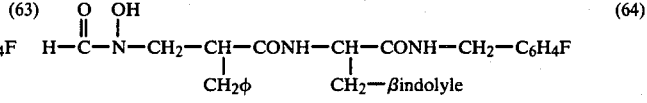(64)
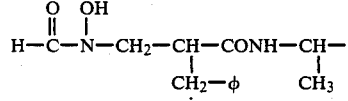(65)
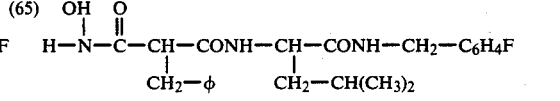(66)
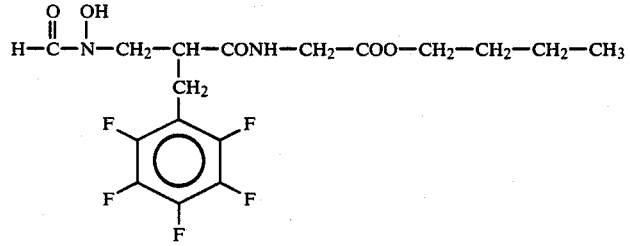(67)
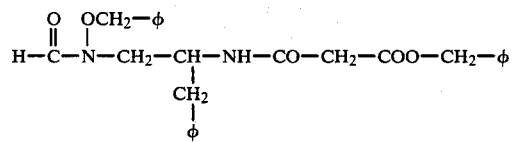(68)
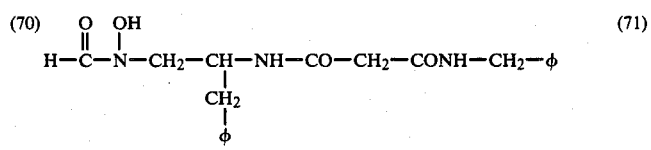(69)
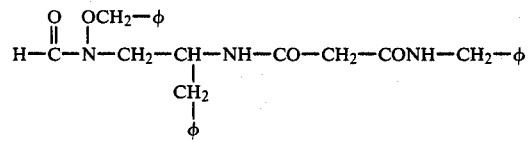(70)
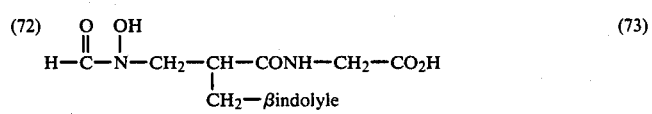(71)
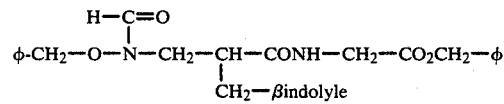(72)
(73)

-continued
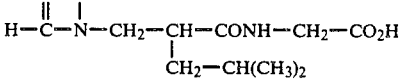  (75)
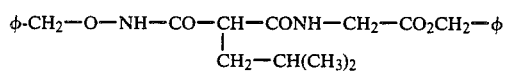  (74)
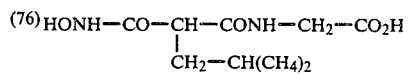  (77)
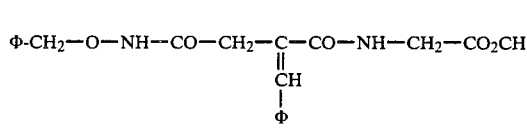  (76)
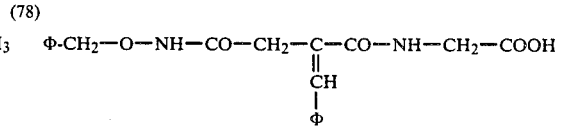  (79)
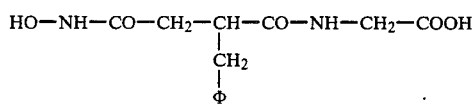  (78)
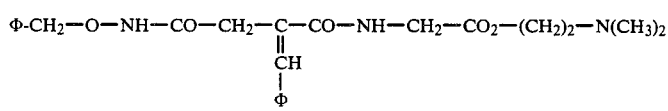  (80)
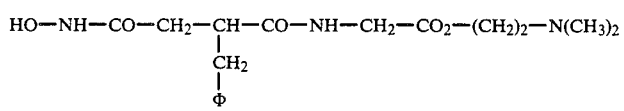  (81)
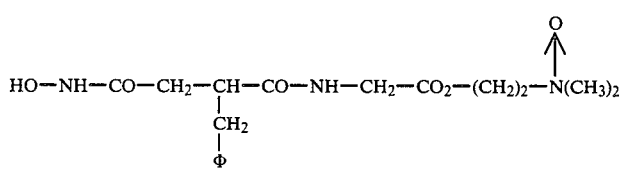  (82)
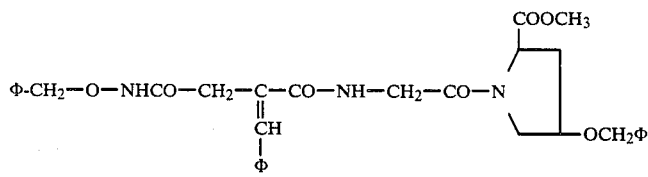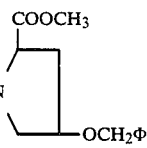  (83)
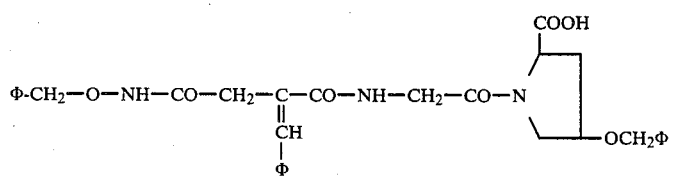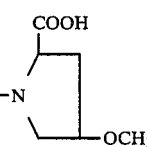  (84)
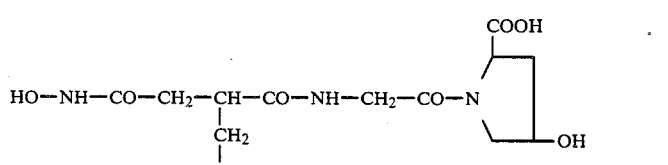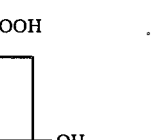  (85)
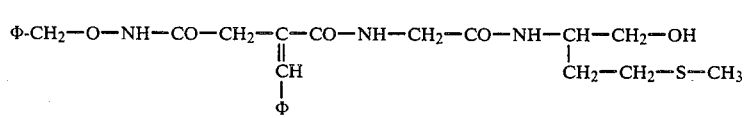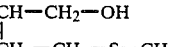  (86)
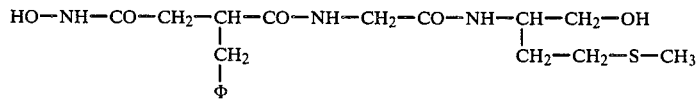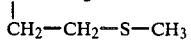  (87)
(88)

-continued

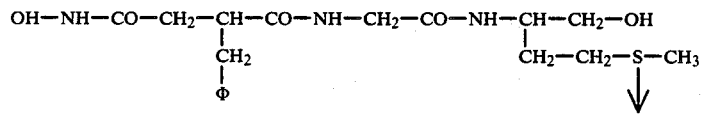

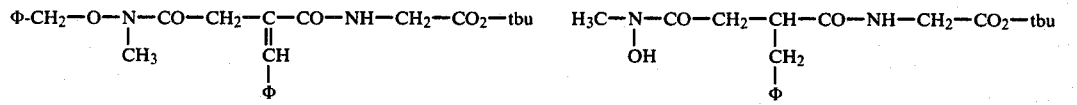
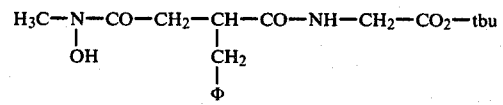

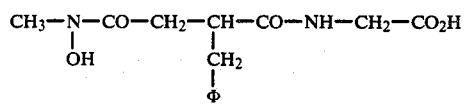
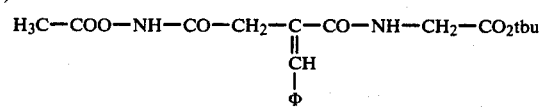

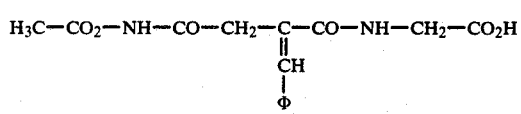
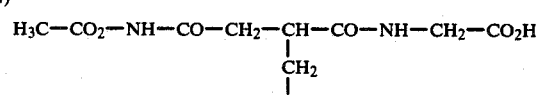

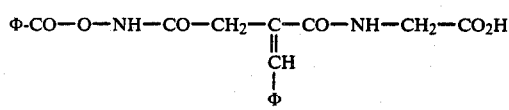
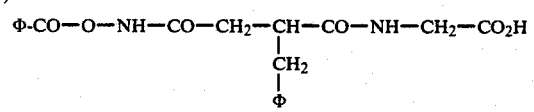

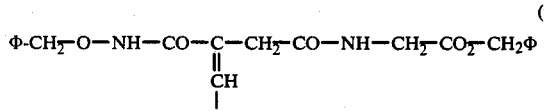
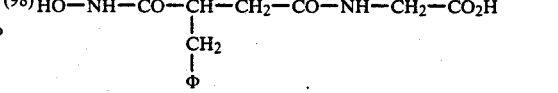

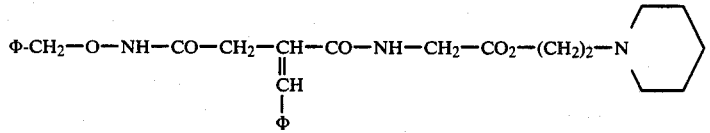

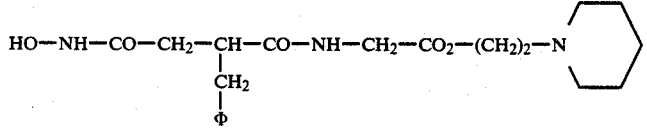

Note that the numbers of the derivatives given above do not correspond to the numbers of the examples which comprise the intermediate steps of synthesis.

The compounds of formula I have one or two asymmetric carbon atoms. They therefore exist in the racemic mixture form or in diastereoisomer forms. All these compounds are within the scope of the present invention. The syntheses described below can employ the racemic mixture or one of the enantiomers as the starting substance. When there is employed in the operational mode of synthesis the racemic starting substance, the stereoisomers obtained may be separated in the product by the conventional chromatographic methods or fractional crystallization methods. Generally, the isomer L relative to the carbon atom of the aminoacid constitutes the preferred isomer form.

The compounds of formula I form salts which are also part of this invention. The salts comprise the acid addition salts which are formed by reaction with various mineral and organic acids providing acid addition salts, comprising, for example, the halohydrates (in particular the hydrochloride and the hydrobromide), sulfate, nitrate, borate, phosphate, oxalate, tartrate, maleate, citrate, acetate, ascorbate, succinate, benzenesulfonate, methanesulfanate, cyclohexane sulfanate, and toluenesulfanate.

The basic addition salts are formed by reaction with bases such as NaOH or by ion exchange reaction.

The salts are formed in a conventional manner by reacting the free form of the product with one or more equivalents of the base or of the appropriate acid providing the desired anion or cation in a solvent or a medium in which the salt is insoluble, or in water and by eliminating the water by lyophilization. By neutralizing the salts with an insoluble acid such as a cation exchanging resin in the hydrogen from [for example the polystyrene-acid-sulfonic resin Dowex 50 ® (Mikes, Laboratory Handbook of Chromatographic Methods (Van Nostrand, 1961), page 256], by eluting with a volatile buffer (for example, pyridine/acetic acid) and extracting with an organic solvent, it is possible to obtain the free formula and, if desired, it is possible to form another salt.

The compounds of the present invention are prepared by the various processes defined below.

The compounds of formula I may be prepared by a conventional peptidic condensation reaction between two suitably protected aminoacid residues.

For example, the functional group or groups (ie. the amino, carboxy, hydroxy groups) which are not involved in the reaction forming the peptide bond (ie. —CONH) in the course of the condensation reaction may be protected by a protector group or protector groups before the condensation reaction.

By way of intermediate protector groups of the amino groups there are employed the usual groups such as t.butoxycarbonyl (Boc), benzyloxycarbonyl (Z), isobornyloxycarbonyl (IBOC) group, etc.).

The carboxylic groups may also be protected, if necessary, by esterification (for example, methyl, ethyl, benzyl esters, etc.).

The condensation reaction is carried out by preferably employing the coupling of the azides without racemization or the process employing dicyclohexyl carbodiimide/1-hydroxy-benzotriazol termed below DCC/HOBt or DCC/3-hydroxy-4-oxo-3,4-dihydro-1,2,3-benzotriazine (OOBt). By way of a modification, the activated esters of the fractions may be employed.

The condensation reaction may be carried out in the presence of a solvent. The solvent may be selected from those known to be of use in peptide condensation reactions. Thus, there may be mentioned, by way of example, the following anhydrous or aqueous solvents: dimethylformamide, dimethylsulfoxide, pyridine, chloroform, dioxane, dichloromethane, tetrahydrofurane, and the appropriate mixtures of such solvents.

The reaction temperature is chosen within the known range for reactions forming peptide bonds, for example normally within the range of from about −20° C. to about 30° C.

Further, the precursor substances (protected peptides) of the desired compounds according to the present invention may also be easily prepared by processes of synthesis in a solid phase.

After the end of the desired condensation reaction, if the product has protector groups, they may be eliminated by the usual processes. Among such processes there may be mentioned: the catalytic reaction in the presence of a catalyst such as palladium black, palladium or carbon, platinum, etc., solvolysis by means of hydrofluoric acid, trifluoroacetic acid, etc. and reduction with metallic sodium in liquid ammonia.

There is employed in particular trifluoroacetic acid (TFA) for eliminating the Boc groups (protector amino) and a saponification for eliminating the protector ester groups of the carboxylic groups.

The compounds of formula I in which X=—NH—PO(OH)$_2$ are obtained in accordance with Li et al, J. Amer. Chem. Soc. (1954), 77, 1866, by the action of dibenzylphosphoryl chloride prepared in accordance with Atherton et al, J. Chem. Soc. (1948) 1106, on the suitable dipeptide acid or ester: R'$_3$ designating the hydrocarbonated fraction corresponds to the ester or acid defined for R$_3$

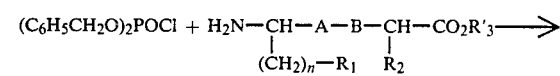

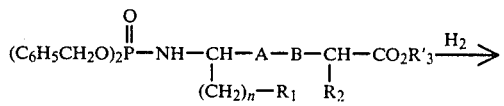

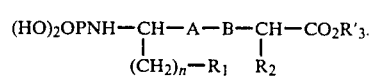

The acid is obtained by deprotection of the benzyl residues upon hydrogenation with Pd/C or PdO.

The phosphonates according to formula I in which X=—PO(OH)$_2$ are obtained by the action of tris-trimethylsilyl phosphite of formula P[OSi(CH$_3$)$_3$]$_3$ in accordance with Rosenthal et al, Tet. Lett. (1975) 977, on a brominated derivative of formula I in which X=Br or CH$_2$Br.

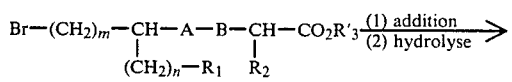

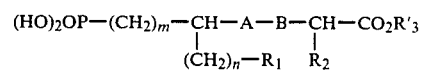

with m=0.1.

The brominated compounds in which m=0 are obtained in accordance with the patent application FR 80/80 601, while the compounds in which m=1 are obtained by the addition of HBr on the derivative:

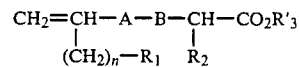

These ethylenic derivatives themselves come from the direct condensation of the suitable substituted acrylic acid with an aminoacid ester:

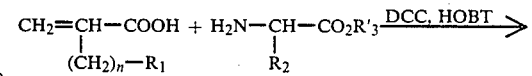

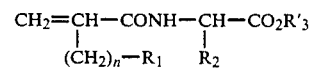

Under mild conditions (20° C.) and in solution in an organic solvent, the peptidic coupling is complete and no addition on the double bond is observed.

The action of anhydrous hydroxylamine on the brominated derivatives of formula I in which X=Br or —CH$_2$Br in accordance with La Noce et al, Ann. Chim. Rome (1968) 58, 393, and Kaminski et al, Roczn, Chem. (1973) 47, 653, gives the corresponding hydroxylamino derivative of formula I in which X=—NHOH or —CH$_2$—NHOH.

The action of sulfurous anhydride SO$_2$ on the preceding hydroxylamino derivatives gives the corresponding sulfamic acids by adaptation of the method of Ryer et al. J. Amer. Chem. Soc. (1951), 5675.

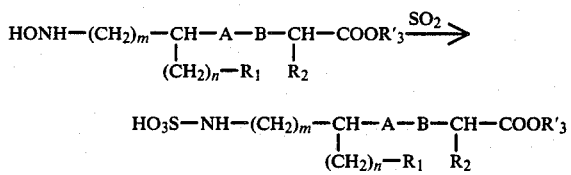

with m=0.1.

The sulfonates corresponding to formula I in which X=—SO₃H or —CH₂SO₃H are obtained in accordance with two channels:

1—Direct addition of bisulfite on ethylenic compound in accordance with the method of Schenck et al, J. Org. Chem. (1951), 16, 1686.

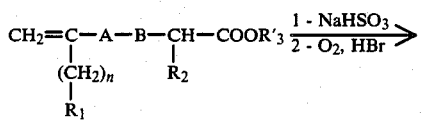

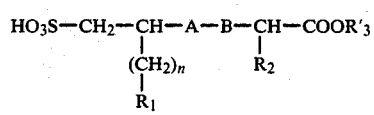

2—Oxidation with oxygen, H₂O₂ or DMSO (Lowe, J. Org. Chem. (1976) 41, 2061) of the corresponding thiols in which X=—SH or —CH₂SH.

The compounds of formula I in which X=—NH₂ or —NHR' are obtained by the direct addition of the suitable amines in accordance with the method of Zilkha, J. Amer. Chem. Soc. (1968) 23, 94.

The compounds of formula I in which

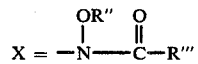

are obtained in two steps, by the action of O.benzylhydroxylamine on bromopropionic acid followed by a condensation of the derivative obtained with an ester or an amide of glycine, or directly by the action of O.benzylhydroxylamine on the derivative of formula

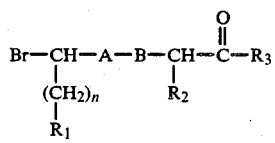

The methods employed are described in the following references:

K. Kaminski and T. Sokolowska, Rocz. Chem. 47, (1973), 653-656

T. Kolasa and A. Chimiak, Tetrahedron, 30, (1974), 3591-95.

In a second step, the derivative obtained having the following formula

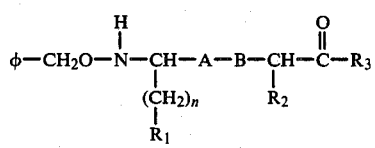

is acylated on the NH group by a suitable R''' Co residue in accordance with the following procedure:

The possible elimination of the residues φ—CH₂ and/or R₃ is effected by hydrogenation and/or treatment with NaOH or TFA (when R₃=Otbu).

The compounds of formula I in which

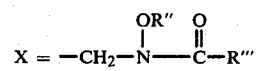

sont obtenus obtained by addition of O.benzylhydroxylamine on an acid of the type

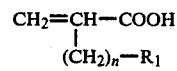

or by substitution with the same reagent of 3-bromo-2-benzyl propionic acid followed by the condensation of the derivative of the following formula:

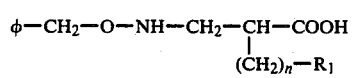

obtained in both cases on a suitable ester or an amide of glycerine.

These derivatives may also be obtained by the direct action of O.benzylhydroxylamine on a dipeptide of the type

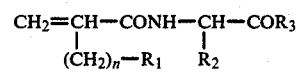

obtained as described above.

The derivative obtained of formula

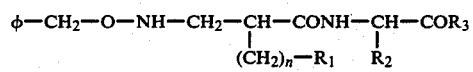

may be acylated by the methods described above and the various groupings eliminated by the conventional methods.

Compounds of formula I in which

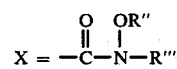

are obtained by condensation of O.benzylhydroxylamine on a suitable malonic ester followed by a saponification.

The compound obtained having formula

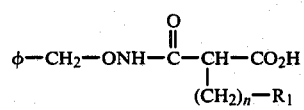

is condensed in accordance with the methods of peptidic synthesis on a suitable amino amide or amino ester so as to obtain the derivative

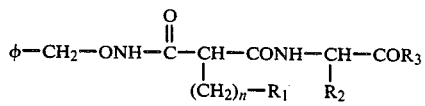

This compound may be alkylated on the HN-benzyloxy group in accordance with the conventional methods.

The compounds of formula I in which

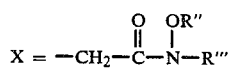

are obtained for example by the action on ethyl α-benzyl mono-succinate of formula

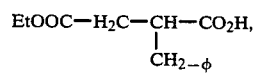

of a suitable amino amide or amino ester.

The compound obtained, having the formula:

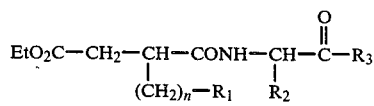

is saponified so as to eliminate the ethyl residue (in the case where $R_3$ is an ester, the group $R_3$ corresponds to Otbu).

The acid obtained is condensed in accordance with the methods of peptidic synthesis with O.benzylhydroxylamine. A derivative having the following formula is obtained:

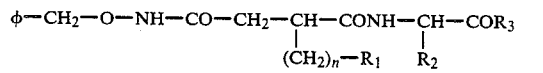

which may be acylated or alkylated on the residue of —O—NH— by conventional methods.

The compounds in which the bond A—B of the general formula (I) is constituted by the groups A=NH, B=CO are obtained by Curtius' inversion from the suitable acid in accordance with the various methods described by Mr. Goodman and Mr. Chorey in *Perspectives in Peptide Chemistry*, Ed. A. Eberlé Karger, Basel (1981) pp. 283–294. Among these there is employed preferbly the method with DPPA in accordance with the typical diagram:

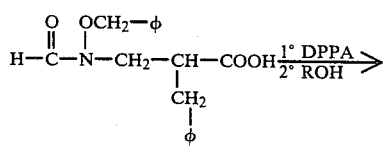

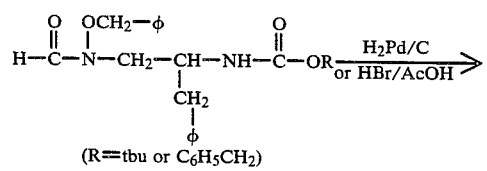

(R=tbu or $C_6H_5CH_2$)

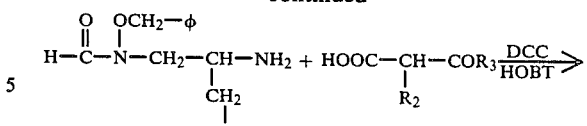

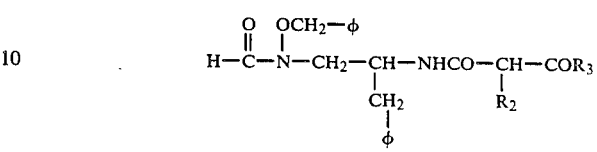

The compounds in which the bond A–B of the general formula (I) is formed by the groups $A=CH_2CO$, $B=NH$ are obtained from ethyl ester of 3-carboxy-4-phenyl-3-buteneoic acid (prepared in accordance with Cohen et al (1968) J.A.C.S., 90, 3495) by the following reactions:

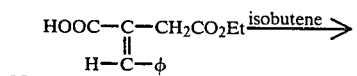

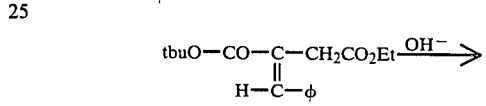

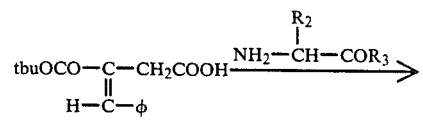

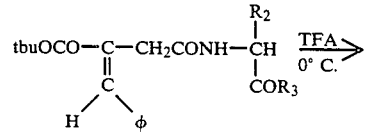

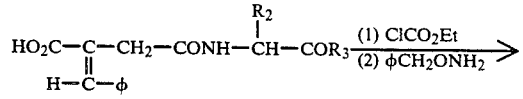

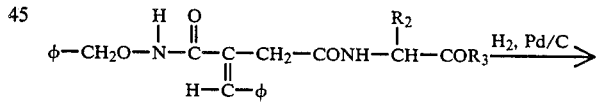

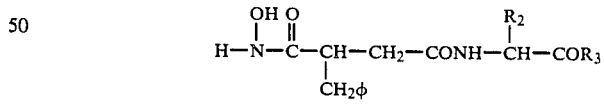

The following examples are given by way of illustration of the preparation of the compounds according to present invention.

EXAMPLE 1

N-(dibenzylphosphoryl) L-phenylalanine-glycine methyl ester (Derivative 1)

2g of L-phenylalanine-glycine methyl ester hydrochloride (7.4 mmoles) are put in suspension in 20 ml of anhydrous chloroform. 1.50 g of triethylamine (15 mmoles) are added. The solid enters into solution. The solution is cooled to 0° C. and 2.17 g (7.4 mmoles) of dibenzyl phosphoryl chloride freshly prepared from dibenzyl phosphite and sulfuryl chloride are added while stirring for 30 minutes. The mixture is allowed to stand for 20 hours at room temperature. The precipitate formed is filtered and the filtrate is washed in succession with 30 ml of 1N HCl, 20 ml of water, 20 ml of 10% bicarbonate, then 2×30 ml of water. The organic solution is dried on anhydrous $Na_2SO_4$ and evaporated under a vacuum. A pale yellow solid is obtained which is recrystallized in ethyl acetate.

W 1.8 g; M.P. 106° C. Structure confirmed by NMR. C,H,N analysis correct.

EXAMPLE 2

N-phosphoryl L-phenylalanine-glycine methyl ester (Derivative 2)

1.5 g of the preceding compound are dissolved in 20 ml of anhydrous methanol and then hydrogenated at ordinary pressure after addition of 0.08 g of palladium oxide. After stirring for 2 hours, the theoretical quantity of nitrogen has been absorbed. This material is filtered, evaporated to dryness under a vacuum. The pasty residue obtained is recrystallized in a 50/50 mixture of ether and hexane.

W 0.62 g; M.P. 138°–145° C.

EXAMPLE 3

N-(dibenzylphosphoryl),N'-(2-methoxycarbonyl acetyl) 1,1-diamino 2-phenyl ethane (Derivative 3)

1 g of N-(2-methoxycarbonyl acetyl) 1,1-diamino 2-phenyl ethane, obtained as described in the description of the patent FR No. 8 008 601, is treated as in Example 1. After washing of the chloroformic solution, a white solid is obtained by evaporation under a vacuum which is crystallized in ether.

M.P. 98°–102° C.; W 0.7 g.

EXAMPLE 4

N-phosphoryl, N'-(2-methoxycarbonyl acetyl) 1,1-diamino 2-phenyl ethane (Derivative 4)

0.5 of the preceding compound in solution in 10 ml of methanol is hydrogenated as in the Example 2. After crystallization in ether, a grey solid is obtained.

M.P. 168°–172° C.; W 0.21 g.

EXAMPLE 5

N-hydroxy L-phenylalanine-glycine (Derivative 5)

4 g of N-(R, 2-bromo 3-phenyl propanoyl)-glycine (14 mmoles) prepared as described in the patent Fr No. 8 008 601, are dissolved in 100 ml of anhydrous ethanol. A 0.5 g (15 mmoles) anhydrous solution of hydroxylamine prepared according to La Noce et al. (1968) Ann. Chim. Rome, 58, 393, in 50 ml of anhydrous ethanol. The mixture is allowed to stand for 48 hours at room temperature, and then evaporated to dryness under a vacuum. The oily residue is dissolved in 20 ml of water and acidified to pH 1 with concentrated HCl. The acid solution is washed with 2×30 ml of $CHCl_3$, then brought to a pH 4 with concentrated $NH_4O_4$ and again extracted wit 30 ml of $CHCl_3$. The organic phases are united, dried and then evaporated to dryness. A glassy solid is obtained which is purified by crystallization in a 50/50 $H_2O$/EtOH mixture.

W 2.8 g; Rf 0.32 in BuOH/AcOH/$H_2O$, 4/1/1 (solvent A)

EXAMPLE 6

N-(2-sulfoamino 3-phenyl propanoyl)-glycine (Derivative 6)

1 g of the compound obtained in Example 5 is dissolved in a mixture of 30 ml of $CHCl_3$ and 20 ml of dioxane. A sulfurous anhydride, $SO_2$, is bubbled through for 5 minutes at 0° C. away from humidity. The gaseous current is stopped and the mixture is allowed to stand at room temperature for 30 minutes. A gelatinous precipitate is formed which is filtered. The filtrate is recrystallized in ethyl acetate.

W 0.168 g; M.P. 237° C.

EXAMPLE 7

N-(2-phosphono 3-phenyl propanoyl)-glycine (Derivative 7)

2 g of N-(R, 2-bromo 3-phenyl propanoyl)-glycine are mixed with, in large excess, 11 g (5 equivalents) of tris-trimethyl silyl phosphite, prepared in accordance with Orlov et al. (1970) Chem. Abstr. 72, 21738 Y, and heated to 100° C. for 20 hours under a nitrogeneous atmosphere. The oily residue obtained is treated with acetonitrile so as to eliminate the excess reagent. A pale brown wax remains which is stirred for 12 hours at room temperature with a 50/50 mixture of tetrahydrofuranne (THF) and water. The precipitate formed is collected, dissolved in methanol and then purified by passage on a column of DEAE cellulose (LH20). 0.186 g of a yellow compound is obtained.

M.P. 250° C.

EXAMPLE 8

N-(2-phosphono 3-phenyl propanoyl)-glycine benzyl ester (Derivative 8)

The preceding reaction carried out with 5 g of N-(R, 2-bromo 3-phenyl propanoyl)-glycine benzyl ester under the same conditions (8 equivalents of the reagent) results in an improved yield of N-(2-phospono 3-phenyl propanoyl)-glycine benzyl ester.

W 2.10 g; M.P. 208°–228° C.

The latter product may be transformed quantitatively into the preceding product by catalytic hydrogenation in the presence of Pd/C in methanol.

EXAMPLE 9

N-(2-sulfo 3-phenyl propanoyl)-glycine (Derivative 9)

3 g (12 mmoles) of N-(S, 2-mercapto 3-phenyl propanoyl)-glycine prepared as described in the patent FR No. 8 008 601, are dissolved in 30 ml of pure dimethylsulfoxide. 0.43 ml of water (24 mmoles) and 0.3 ml of a 48% solution of HBr are added. The mixture, placed in a three-neck flask equipped with a distillation head, is slowly brought to the temperature of 100°–110° C. The dimethylsulfide formed in the course of the reaction distills at 40°–45° C. When the distillation stops (about 3 hours), there is added 2N NaOH to the liquid residue of the three-neck flask until pH 9. The addition of 100 ml of ethyl acetate results in the precipitation of 1.4 g of sodium salt. The latter is recrystallized in a 50/50 methanol/$H_2O$ mixture.

W 0.9 g; M.P. 300° C.

This compound may also be obtained with a lower yield by oxidation of the N-(S, 2-mercapto 3-phenyl propanoyl)-glycine in accordance with the method of Vasilevskii et al., Z. Org. Khimil, (1970), 244.

EXAMPLE 10

N-(2-sulfo, 3-phenyl propanoyl)-glycine benzyl ester (Derivative 10) 2 g of N-(S, 2-mercapto 3-phenyl propanoyl)-glycine benzyl ester obtained as described in the patent FR No. 8 008 601, are treated under the same conditions as before. However, at the end of the reaction, the residue of the three-neck flask is diluted in 50 ml of water and separated from the residual DMSO by chromatography on 50-X8 Dowex resin in the acid form. The fractionating is followed by a thin layer-chromatography (CMC) on a silica gel plate. Eluent (BuOH/AcOH/H$_2$O, 4/1/1, iode developer.

The fractions of Rf=0.61 are united, evaporated under reduced pressure. The wax obtained is crystallized in boiling ethyl acetate.

W 0.42 g; M.P. 260°–280° C.

EXAMPLE 11

N-(2-benzyl propenoyl)-glycine benzyl ester 2.42 g (15 mmoles) of 2-benzyl acrylic acid are dissolved in 30 ml of THF and 10 ml of CHCl$_3$. There is added a solution in 50 ml of THF of 1.87 g of glycine benzyl ester hydrochlorate, 2.2 g of triethylamine, then 2.20 g of HOBT and 3.4 g of DCC. The mixture is stirred for 20 hours at room temperature. The precipitate of DCU formed is collected. After evaporating to dryness and taking up with ethyl acetate the organic phase is washed in succession with 2×20 ml of citric acid, then 3×20 ml of NaHCO$_3$. The material is concentrated under a vacuum and the rest of the DCU formed is suction filtered. A yellow oil which crystallizes slowly is obtained.

W 2.3 g; M.P. 60° C.

EXAMPLE 12

N-(2-benzyl propenoyl)-glycine 2.10 (6.8 mmoles) of N-(2-benzyl propénoyl-glycine benzyl ester, M.P. =60° C, are stirred at 10° C. for 2 hours with a mixture of 30 ml of methanol and 0.27 g of NaOH (6.8 mmoles), dissolved in 5 ml of water. The pH is brought to 1 by the addition of 2N HCl and the material is extracted with ethyl acetate. The solvent is washed with 2×20 ml of water, dried and evaporated under a vacuum. 1.36 g of crystals are obtained.

M.P. 82° C. Rf 0.78 in CHCl$_3$/Me OH, 9/1.

This compound may be obtained by the condensation of 2-benzyl acrylic acid with glycine methyl ester followed by saponification in accordance with the following technique.

4.86 g (30 mmoles) of 2-benzyl acrylic acid are dissolved in 50 ml of dry THF. There are added in succession a solution of 3.76 g of glycine methyl ester hydrochlorate (1 equivalent) and 4.2 ml of triethylamine (1 equivalent), then a solution of 4.59 g of HOBT and 6.8 g of DCC in 40 ml of THF. The mixture is stirred for 18 hours at 25° C. The DCU formed is filtered, evaporated to dryness and taken up with ethyl acetate. It is washed with 2×20 ml of citric acid, then 3× of NaHCO$_3$ and 2×20 ml of water. The material is dried on Na$_2$SO$_4$ and concentrated under a vacuum. The remaining DCU is drained. A pale yellow oil is obtained.

W 6.67 g; Rf 0.43 in CHCl$_3$/MeOH, 9/1.

6.57 g of N-(2-benzyl propenoyl-glycine methyl ester obtained are stirred for 2 hours at room temperature in a solution of 25 ml of NaOH and 28.2 ml of 1N NaOH. The methanol is evaporated, 5 ml of water are added, and the mixture is acidified with 2N HCl to pH 1, extracted with ethyl acetate. After evaporation, 6.17 g of acid 12 are obtained.

M.P. 82° C.

EXAMPLE 13

N-(2-benzyl propenoyl)-glycine 2-trifluoro ethyl ester

Obtained as in Example 11 by replacing the glycine benzyl ester by trifluoro ethyl ester obtained by the action of SO$_2$Cl on a solution of glycine in trifluoroethyl alcohol.

Pale yellow oil. Rf 0.62 in CHCl$_3$/MeOH.

EXAMPLE 14

N-(2-benzyl propenoyl)-glycine p. fluorobenzyl ester

Obtained as in Example 11 by condensing the 2-benzyl acrylic acid with p. fluorobenzyl ester.

Yellow oil. Rf 0.72.

EXAMPLE 15

N-(3-bromo 2-benzyl propanoyl)-glycine benzyl ester 3 g of N-(2-benzyl propenoyl)-glycine benzyl ester (Example 11) are dissolved in 20 ml of dry CHCl$_3$. There are added away from humidity and at 0° C. 20 ml of a solution of HBr (3 equivalents), obtained by dissolution of gaseous HBR. The mixture is stirred for 1 hour at 0° C. and then for 10 hours at room temperature. It is concentrated to 10 ml under a vacuum, and 20 ml of water are added and the mixture is extracted with 2×30 ml of CHCl$_3$. The organic phase is washer with 20 ml of saturated NaHCO$_3$ solvent, then with 2×20 ml of water. The material is dried on Na$_2$SO$_4$ and evaporated to dryness. The white solid obtained is crystallized in ether.

W 2.10 g; M.P. 151° C.

EXAMPLES 16 AND 17

The method of Example 15 is applied to the compounds of Examples 13 and 14 so as to obtain N-(3-bromo 2-benzyl propanoyl)-glycine trifluoroethyl, 16, and p.fluorobenzyl, 17, esters.

EXAMPLE 18

N-(3-hydroxyamino, 2-benzyl propanoyl)-glycine benzyl ester(Derivative 11) 1.2 g of the compound of Example 15 is treated as in the Example 5 with anhydrous hydroxylamine. After stirring for 20 hours, the mixture is evaporated under a vacuum. The extraction as in Example 5 provides 0.45 g of an amorphous compound.

Rf 0.62 in BuOH/AcOH/H$_2$O, 4/1/1.

EXAMPLES 19 AND 20

The method of Example 18 applied to the compounds of Examples 16 and 17 respectively provides N-(3-hydroxyamino 2-benzyl propanoyl)-glycine, ethyl trifluoro ester, 19, and N-(3-hydroxyamino 2-benzyl propanoyl)-glycine p.fluorobenzyl ester, 20.

EXAMPLE 21

N-(3-sulfoamino, 2-benzyl propanoyl)-glycine p.fluorobenzyl ester (Derivative 14)

0.25 g of the compound 20 treated with sulfurous anhydride SO$_2$, in accordance with the method described in Example 6, results in the derivative of the following sulfamic acid: N-(3-sulfoamino 2-benzyl propanoyl)-glycine p.fluorobenzyl ester.

W 0.160 g; M.P. 260° C.

EXAMPLE 22

N-(3-phosphono 2-benzyl propanoyl)-glycine benzyl ester(Derivative 15)

0.7 g of N-(3-bromo 2-Benzyl propanoyl)-glycine p.fluorobenzyl ester (example 17), are treated as in Example 7.

0.18 g of N-(3-phosphono 2-benzyl propanoyl)-glycine benzyl ester are obtained.

Yellow product. M.P. 250° C.; Rf 0.32 in BuOH-/AcOH/H$_2$O, 4/1/1.

EXAMPLE 23

N-(3-sulfo 2-benzyl propanoyl)-glycine benzyl ester (Derivative 16)

4 g (13 mmoles) of N-(2-benzyl propenoyl)-glycine benzyl ester 11 are dissolved in a mixture of 10 ml of CH$_3$OH and 50 ml of water containing 0.37 g of Na$_2$SO$_4$ (3 mmoles) and 1.04 (10 mmoles) of NaHSO$_3$. The flask is then connected to a hydrogenation apparatus operating at ordinary pressure and filled with oxygen. After sweeping, the flask with the oxygen, the reaction is magnetically stirred. After stirring for 20 hours, 10.5 ml of oxygen were absorbed. The solution is evaporated under a vacuum to a volume of 10 ml then extracted with 2×20 ml of ethyl acetate. The dried solvent is evaporated to dryness under a vacuum. An amorphous solid is obtained which is recrystallized in methanol. In this way 1.7 g of the sodium salt of Example 23 are obtained. M.P. 260° C.

This compound may also be obtained by oxidation with DMSO according to the method described for the compound 10, in starting with N-(3-mercapto 2-benzyl propanoyl)-glycine benzyle ester.

EXAMPLE 24

3-ethylamino 2-benzyl propanoyl glycine benzyl ester (Derivative 17)

4 g (13 mmoles) of N-(2-benzyl propenoyl)-glycine p.fluorobenzyl ester, 14, are dissolved in 15 ml of pyridine. 1.02 g (13 mmoles) of ethylamine in solution in the pyridine are added. The solution is heated to 120° C. for 2 hours. At the end of the reaction, the solution is concentrated to 5 ml, and 50 ml of ether are added. A white product precipitates. It is filtered, washed with water, and then with ether. It is recrystallized in a 50/50 CH$_3$OH/H$_2$O mixture. White crystals are obtained.

W 1.8 g; Rf 0.81 in BuOH/AcOH/H$_2$O. 4/1/1.

EXAMPLE 25

N-hydroxy L-alanine-glycine (Derivative 18)

3 g of N-(R, 2-bromo propanoyl)-glycine obtained by condensation of 2-bromo propionic acid (prepared according to E. Fischer et al., Annalen, 357, 1 (1907) with the glycine are dissolved in 100 ml of anhydrous ethanol and stirred for 48 hours with anhydrous hydroxylamine according to Example 5.

0.7 g of a white solid is obtained after crystallization in boiling ethanol.

M.P. 260°–270° C.

EXAMPLE 26

N-(2-sulfoamino propanoyl)-glycine (Derivative 19)

A current of SO$_2$ is bubbled in 0.5 g of the preceding compound dissolved in a mixture of 10 ml of CHCl$_3$ and 10 ml of dioxanne. After treatment as in Example 6, 0.130 g of a solid is obtained.

M.P. 210°–230° C.

EXAMPLE 27

N-(dibenzylphosphonyl) L-alanine-L-thioproline 2-trifluoro ethyl ester (Derivative 20)

4 g of 4-carboxy thiazolidine are dissolved in 20 ml of trifluoroethanol. 2 ml of SOCl$_2$ are added and the mixture is refluxed for 15 mn. After having allowed to stand 20 hours at 25° C. 3.2 g of 4-carboxy thiazolidine trifluoro-ethyl ester hydrochlorate are drained off.

The coupling between the t.boc L-alanine and the preceding ester is effected by means of the DCC+HOBT mixture according to conventional techniques. The compound obtained is deprotected with the TFA and yields after evaporation and washing with ester 3.7 g of L.Ala-L.thioproline trifluoroethyl ester.

2 g of L-Ala-L.thioproline trifluoroethyl ester trifluoroacetate (5.1. mmoles) are put in suspension in 30 ml of dry CHCl$_3$. There is added at 0° C. a mixture of 1.5 g (5.1 mmoles) of freshly prepared dibenzylphophoryl chloride, then 1.02 g of triethylamine in 2 ml of dry CHCl$_3$. The mixture is stirred for 20 hours at room temperature. The precipitate formed is filtered. The organic phase, treated as in Example 1, yields a white solid.

Y 2.20 g; M.P. 143°–148° C.

EXAMPLE 28

N-phorphoryl L-alanine-thioproline trifluoroethyl ester (Derivative 21)

1.8 of the preceding compound are dissolved in 31 ml of dry methanol and hydrogenated at ordinary pressure in the presence of 1 g of 10% Pd/C. After 10 hours, the theoretical quantity (2 equivalents) of H$_2$ were had been absorbed. The material is filtered, evaporated under a vacuum and taken up with methanol and chromatographed on cephade×LH 20 in CH$_3$OH. 1.1 g of a vitrous white solid, soluble in water, is obtained.

M.P. 250° C.; Rf 0.82 in BuOH/AcOH/H$_2$O, 4/1/1.

EXAMPLE 29

2-bromo-3-phenyl-propanoyl glycine isoamylamide

There are placed in a flask of one liter 11.56 g of 2-bromo-3-phenyl propanoic acid in 50 ml of dry THF. There are added in succession at 5° C., 6.34 g of glycine methyl ester hydrochlorate and 5.1 g of triethylamine, then 7.73 g of HOBT in 50 ml of THF, and finally 10.42 g of DCC in 50 ml of CHCl$_3$. The mixture is stirred for 72 hours at 25° C. The DCU formed is filtered and concentrated under a vacuum. The solid residue is taken up with 100 ml of ethyl acetate. The solution is washed in succession with 50 ml of H$_2$O, then with 2×20 ml of 10% of citric acid and finally with 2×20 ml of 10% NaHCO$_3$. The organic solution is dried on dry Na$_2$SO$_4$ and then evaporated under a vacuum. The cyrstalline precipitate is recrystallized with AcOEt.

W 11.2 g; M.P. 116° C.; Rdt 74%

Analysis C,H,N—NMR in conformity—Rf 0.53 in CHCl$_3$/CH$_3$OH, 9/1.

2 g of the preceding methyl ester are placed in 20 ml of THF. There are added in succession at 0° C., 0.61 g of isoamylamine in 10 ml of CHCl$_3$, then 1.87 g of HOBT, H$_2$O, and 1.44 g of DCC in 10 ml of CHCl$_3$. The mixture is stirred for 12 hours at room temperature. The precipitate of DCU is drained off, the solvent evaporated to dryness under a vacuum gives a syrupy residue which is taken up with 2cOEt (50 ml). The organic solution is washed as before with citric acid, bicarbonate and water. After evaporation to dryness and crystallization in AcOEt, 2.34 g of a white solid are obtained.

M.P. 110° C.; Rdt 94%; NMR correct C,H,N

EXAMPLE 30

N-(2-bensyloxyamino 3-phenyl propanoyl)-glycine isoamylamide (Derivative 22)

1.78 g of the preceding amide are dissolved in 20 ml of MeOH. 1.60 g of O.benzylhydroxylamine Hydrochlorate and 2.59 g of diisopropylethyl amine are then added. The mixture is refluxed for 8 days. The mixture is concentrated to dryness under a vacuum, and taken up with AcOEt (30 ml), the precipitate of diisopropyl ethylamine salts is filtered. The solvent is evaporated under a vacuum and results in an oil (2.61 g) which is purified on a silica column with the CHCl$_3$/CH$_3$OH, 98/2 mixture as eluent.

1.04 g of oily product are obtained.
NMR correct C,H,H.

EXAMPLE 31

N-(N-benzyloxy 2-formamido 3-phenylpropanoyl)-glycine isoamylamide (Derivative 23)

0.42 g of the preceding compound is added to 5.2 ml of formic acid (d=1.23). The mixture is cooled to 0° C., 0.52 ml of acetic anhydride is added, and the mixture is stirred for 2 hours at room temperature and concentrated to dryness under a vacuum. The oil is purified by passage of a silica gel column with MeOH as eluent. The fractions of Rf=0.32 in CHCl$_3$/CH$_3$OH, 95/5 are united and evaporated to dryness. 0.22 g of a pale yellow oil is obtained.

NMR correct C,H,N.

EXAMPLE 32

N-(N-hydroxy 2-formamido 3-phenyl propanoyl)-glycine isoamylamide (Derivative 24)

127 mg of the compound of Example 31 are dissolved in 3 ml of the mixture CH$_3$OH/AcOH/H$_2$O, 4/5/1 and hydrogenated at ordinary pressure in the presence of 30 mg of 10% Pd/C. After 1 hour, the theoretical volume is absorbed or filtered, and concentrated to dryness giving a white solid. W 88 mg.

Rdt 88%; Rf 0.85; BuOH/AcOH/H$_2$O, 4/1/1.

EXAMPLE 33

(a) N-benzyloxy 2-formamido 3-phenyl propanoic acid 0.5 g of N-benzyloxy phenylalanine (obtained by the action of O.benzylhydroxylamine on 2-bromo 3-phenyl propanoic acid, according to La Noce et. al., Ann. Chim. Rome, 1968, 58, 393), is added to 9.2 ml of HCO$_2$H. 0.5 ml of acetic anhydride are poured onto the mixture which is stirred for 3 hours at 0° C. It is concentrated to dryness under a vacuum. The resinous solid is cyrstallized in EtOH.

W 500 mg; Rdt 90%; M.P. 186° C.; Rf 0.55 in CHCl$_3$/CH$_3$OH, 5/1. NMR correct C,H,N.

(b) N-(N-benzyloxy 2-formamido 3-phenyl propanoyl glycine benzyl ester (Derivative 25)

0.49 g of the preceding compound are added to 0.552 0.552 g of glycine benzyl ester tosylate in the presence of 0.165 g of triethylamine. There are then added 0.25 g of HOBT, H$_2$O in 10 ml of THF, then 0.69 g of N-cyclohexyl-N'-[2-(4-morpholinoethyl)] carbodiimide tosylate. The mixture is stirred overnight at room temperature, the DCU formed is filtered and the solution is concentrated to dryness and taken up with AcOEt. The remaining DCU is filtered and treated as in Example 29. 0.50 g of a thick oil is obtained.

Rdt 68%; Rf 0.74 in CHCl$_3$/AcOH, 9/1/0.5 NMR correct. Product employed crude.

EXAMPLE 34

N-(N-hydroxy 2-formamido 3-phenyl propanoyl)-glycine (Derivative 26)

477 mg of the preceding compound are hydrogenated under the conditions of Example 32. 263 mg of product are obtained.

Rdt 92% of a solid; M.P. 203° C.; NMR correct; C,H,N,O.

EXAMPLE 35

(a) (N-2-benzyloxycarbomoyl 3-phenyl propanoic acid 1.5 g of the ethyl monoester of the ethyl benzylmalonate are coupled with 1.08 g of O-benzylhydroxylamine, HCl under the conditions of the peptic synthesis (Example 29). After treatment as for the compound 29, there are obtained 2.17 g (Rdt: 98%) of a pale yellow oil which is saponified without purification with 20 ml of 1N NaOH in 15 ml of EtOH for 8 hours at 5° C. A slightly insoluble part is filtered, the EtOH is evaporated, and the aqueous phase is extracted with 1N HCl to pH 2-3. The product crystallizes into white paillettes.

M.P. 180° C.; W 1.25 g Rdt 64%; NMR correct, C,H,N.

(b) N-[2-(N-benzyloxy carbamoyl) 3-phenyl propanoyl]-glycine benzyl ester (Derivative 27)

0.5 g of the compound obtained at (a) is coupled with 0.56 g of glycine benzyl ester according to the conditions of Example 33b. After treatment, 0.56 g of product is obtained.

Rdt 75% of an amorphous white solid; M.P. 70° C.; NMR; C,H,N.

EXAMPLE 36

N-[2-(N-hydroxy carbamoyl) 3-phenyl propanoyl]-glycine (Derivative 28)

0.5 g of the compound 35 are hydrogenated under the conditions of Example 32. 274 mg of product are obtained.

M.P. 183° C.; RF 0.47 in A.

EXAMPLE 37

N-[2-(N-benzyloxy carbamoyl) 3-phenyl propanoyl]-glycine methyl ester (Derivative 29)

0.6 g of the compound 35a is combined in accordance with the usual method (Example 33b) with 0.25 g of glycine methyl ester hydrochloride. After conventional treatment (Example 33b) 0.74 g of a white solid is obtained.

M.P. 107° C. (EtOH); Rdt 64%; Rf 0.7 in CHCl$_3$/CH$_3$OH/AcOH, 0/1/0.5; NMR correct; C,H,N

EXAMPLE 38

N-[2-(N-hydroxy carbamoyl) 3-phenyl propanoyl]-glycine methyl ester (Derivative 30)

0.4 g of the compound 37 is hydrogenated at ordinary pressure under the conditions of Example 32. 242 mg of a white solid are obtained.

M.P. 174° C.; Rdt 80%; Rf 0.44 in (B) CHCl$_3$/CH$_3$OH/AcOH, 0/1/0.5

EXAMPLE 39

N-[2-(N-benzyloxy carbamoyl) 3-phenyl propanoyl]-glycine (Derivative 31)

0.368 g of the compound 35a are combined with 0.32 g of glycine benzylamide trifluoroacetate under the conditions of Example 33b. 0.47 g of a white solid is obtained.

M.P. 140° C.; Rdt 88%; Rf 0.63 in (B); NMR correct; C,H,N.

EXAMPLE 40

N-[2-(N-hydroxy carbamol 3-phenyl propanoyl]-glycine (Derivative 32)

0.25 g of the preceding compound are hydrogenated under the conditions of Example 32. 0.20 g of a white solid is obtained.

M.P. 166° C.; Rdt 87%; Rf 0.84 in (A); NMR correct; C,H,N.

EXAMPLE 41

N-[2-(N-benzyloxy carbamoyl) 3-phenyl propanoyl]-glycine isoamylamide (Derivative 33)

0.7 g of the compound 35a are combined with 0.65 g of glycine isoamylamide trifluoroacetate under the conditions of Example 34. 0.94 g of white crystals is obtained.

M.P. 143° C.; Rdt 88%; Rf 0.95 in (A) NMR correct; C,H,N.

EXAMPLE 42

N-[2-(N-hydroxy carbamoyl) 3-phenyl propanoyl]-glycine isoamylamide (Derivative 34)

0.4 of the preceding compound is hydrogenated under the conditions of Example 32. 0.30 g of white crystals is obtained.

M.P. 186° C.; Rdt 90%; Rf 0.84 in (B).

EXAMPLE 43

(a) 3-benzyloxyamino 2-benzyl propanoic acid 5.07 g of triethylamine is added at 0° C. while stirring to a solution of 7.87 g of O.benzylhdroxylamine hydrochloride in a mixture of 50 ml of water and 50 lf of CHCl$_3$. The organic phase is separated out, washed with 3×50 ml of water, dried and evaporated under a vacuum. 6 g of O.benzylhydroxylamine base are obtained. The latter is added away from air in solution in 20 ml of MeOH to a solution of 2 g of 2-benzyl acrylic acid in 10 ml of MeOH. The mixture is refluxed for 7 days and concentrated under a vacuum. The oil obtained is dissolved in 100 ml of AcOEt and N NaOH is added until a pH 10 is reached. The aqueous phase is decanted and acidified with N HCl until a pH 1-2 is reached. The acid phase is extracted with AcOEt (2×50 ml), dried and evaporated under a vacuum. The oil obtained slowly crystallizes.

M.P. 40° C.; W 1.6 g; Rdt 46%; Rf 0.47 in CHCl$_3$/MeOH, 9/1; NMR correct; C,H,N.

(b) 3-(N-benzyloxy formamido) 2-benzyl propanoic acid 1.08 g of the preceding compound are added to 19 ml of HCO$_2$H (d=1.23). 1.9 ml of acetic anhydride are poured at 0° C. while stirring. The mixture is stirred for 5 hours at 0° C. and concentrated to dryness under a vacuum. The thick oil is triturated in n-hexane. A solid is obtained.

M.P. <40° C.; Rf 0.6 in CHCl$_3$/CH$_3$OH, 9/1; W 1.2 g; Rdt 100%; NMR correct.

The compound is employed without subsequent purification for the couplings.

(c) N-[N-benzyloxy 3-formamido 2-benzyl propanoyl]-glycine isoamylamide (Derivative 35)

0.15 g of the compound obtained at (b) in solution in 15 ml of dry THF is added to 0.12 g of glycine isoamylamide trifluoroacetate and 0.048 g of triethylamine in 20 ml of THF. There are added in succession to the mixture 73 mg of HOBT in 5 ml of THF, then 0.2 g of DCC (tosylate) in ml of THF. The solution obtained is stirred for 12 hours at room temperature. The mixture is treated as in Example 29. The oil obtained (98 mg) is chromatographed on a silicon gel column (eluent CH$_3$OH/CHCl$_3$ 2/98). 64 mg of oil are obtained.

RF 0.28 in CHCl$_3$/MeOH, 9/1; Rdt 30%; NMR correct.

EXAMPLE 44

N-(N-hydroxy 3-formamido 2-benzyl propanoyl)-glycine isoamylamide (Derivative 36)

60 mg of the preceding compound are hydrogenated as in Example 32. 33 mg of a white solid are obtained.

Rdt 70%; Rf 0.52 CHCl$_3$/MeOH, 9/1; NMR correct; C,H,N.

EXAMPLE 45

N-(N-benzyloxy 3-formamido 2-benzyl propanoyl)-glycine benzyl ester (Derivative 37)

0.15 g of the derivative 43b in solution in 20 ml of dry THF are reacted with 0.16 g of glycine benzyl ester tosylate under the conditions similar to Example 45c. After successive washings, 0.21 g of a thick oil is obtained.

Rdt 97%; RF 0.7 (b), NMR correct; C,H,N.

EXAMPLE 46

N-(N-hydroxy 3-formamido 2-benzyl propanoyl)-glycine (Derivative 38)

0.19 g of the preceding compound is hydrogenated at ordinary pressure under the conditions of Example 32. 103 mg of white solid are obtained.

M.P. 182° C.; Rf 0.52 in (A)

EXAMPLE 47

N-(N-benzyloxy 3-formamido 2-benzyl propnaoyl)-glycine methyl ester (Derivative 39)

0.6 g of the compound 43b is reacted under the conditions of the peptidic coupling (Example 29) with 0.24 g of the glycine methyl ester (hydrochloride). After the usual treatments, 0.36 g of an oil is obtained.

Rdt 50%; Rf 0.77 in CHCl$_3$/CH$_3$OH, R/1.

The compound is employed without subsequent purification for preparing the derivative 48.

EXAMPLE 48

N-(N-hydroxy 3-formamido 2-benzyl proanoyl)-glycine methyl ester (Derivative 40)

0.30 g of the derivative 47 is hydrogenated at ordinary pressure as in Example 32. 226 mg of a white solid are obtained.

RDT 98%; Rf 0.51 in CHCl$_3$/CH$_3$OH, 5/1; NMR correct; C,H,N.

EXAMPLE 49

(a) 3-(N-benzyloxy acetamido) 2-benzyl propanoic acid 0.4 g of the compound 43a is dissolved in 7 ml of pyridine. 0.7 ml of acetic anhydride is added at 0° C. After stirring for 5 hours at room temperature, the mixture is concentrated to dryness under a vacuum and triturated with ethyl ether. After decantation, 0.412 g of a thick oil is obtained.

Rf 0.69 in CHCl$_3$/CH$_3$OH, 5/1; Rdt 93%; NMR correct; C,H,N.

(b) N-(N-benzyloxy 3-acetamido 2-benzyl propanoyl)-glycine benzyl ester (Derivative 41)

0.52 g of the preceding compound is dissolved in 20 ml of dry THF and treated under the conditions of the peptidic coupling with 0.56 g of glycine benzyl ester tosylate. After treatment as in Example 29, 0.42 g of a lac is obtained.

RF 0.81 in CHCl$_3$/CH$_3$OH, 5/1; Rdt 53%; NMR correct; C,H,N.

EXAMPLE 50

N-(N-hydroxy 3-acetamido 2-benzyl propanoyl)-glycine (Derivative 42)

0.2 g of the preceding compound is hydrogenated at ordinary pressure as in Example 32. 120 mg of a white solid are obtained.

Rdt 100%; M.P. 176° C.; Rf 0.5 in (A); NMR correct; C,H,N.

EXAMPLE 51

N-(N-benzyloxy 3-acetamido 2-benzyl propanoyl)-glycine benzylamide (Derivative 43)

0.4 g of the compound 49a is coupled under the conditions of Example 29 with 0.35 g of benzylamide glycine trifluoroacetate. After the usual treatments 0.28 g of a solid is obtained.

M.P. 82° C.; Rdt 46% ; RF 0.73 in CHCl$_3$CH$_3$OH, 5/1; NMR correct; C.H.N.

EXAMPLE 52

N-(N-hydroxy 3-acetamido 2-benzyl propanoyl)-glycine benzylamide 0.2 g of the preceding compound is hydrogenated at ordinary pressure under the conditions of Example 32. After treatment, 136 mg of white crystals are obtained.

M.P. 147° C.; Rdt 84%; Rf 0.58 in CHCl$_3$/CH$_3$OH; MMR correct; C.H.N.

EXAMPLE 53

N-(3-ethoxycarbonyl 2-benzyl propanoly)-glycine tertiobutyl ester 7 g of 3-ethoxycarbonyl 2-benzyl propanoic acid (0.03 mole) prepared in accordance with S. G. COHEN (U.A.C.S., 90, 3495–3502, 1968) are dissolved in a mixture of 30 ml of dry THF and 10 ml of anhydrous DMF. There are added in succession while stirring at 0° C. 7.5 g of glycine tertiobutylic ester trifluoroacetate and 3.1 g of triethylamine in 10 mlg of THF, then 4.02 g of HOBT and 5.40 g of DCC in 20 ml of THF. The mixture is stirred for 12 hours at room temperature and the DCU formed is filtered and concentrated to dryness under a vacuum. A syrupy residue is obtained which is taken up with 100 ml of AcOET. A new precipitate of DCU is filtered and the organic solution is washed with 10% of citric acid (3×20 ml), 10% NaHCO$_3$ (3×20 ml) and then once with 30 ml of water. The solution is dried and evaporated under a vacuum and a pale yellow oil is obtained.

Rf 0.61 in (B); W 8.1. g; Rdt 82%; NMR correct; C,H,N.

EXAMPLE 54

N-(3-carboxy 2-benzyl propanoyl)-glycine tertiobutyl ester 5 g of the preceding compound are dissolved in 10 ml of the mixture, 5 ml of CH$_3$OH, 20 ml of water. 1 ml of NaOH is added and the mixture is stirred for 4 hours at room temperature. A slightly insoluble part is filtered off and extracted once with 50 ml of ether. The alkalyne aqueous phase is acidified to pH 1-2 with N HCl and extracted with 3×20 ml of AcOEt. The organic phases are combined, washed with water (2×20 ml) then dried and evaporated to dryness under a vacuum. A white solid is obtained which is recrystallized in MeOH-/EtOH, 20/80.

W 4.0 g; Rdt 87%; M.P. 92°–95° C.; Rf 0.76 (A) NMR correct; C,H,N.

EXAMPLE 55

N-(N-benzyloxy 3-carbamoyl 2-benzyl propanoyl)-glycine tertiobutyl ester (Derivative 45)

2.0 g (6.5 mmoles) of the preceding derivative are dissolved in 20 ml of THF and 50 ml of DMF. 1.0 g of 0 benzylhydroxylamine hydrochloride in 10 ml of CHCl$_3$ is added, then there are added in succession 0.65 g of of triethylamine, 1 g of HOBT, H$_2$O and 1.25 g of DCC in solution in 10 ml of CHCl$_3$. The mixture is stirred for 12 hours at room temperature, the DCU is filtered and evaporated under a vacuum to dryness and taken up with 50 ml of AcOEt and the washings are carried out as in Example 29. In this way 2.1 of a colourless oil are obtained.

Rdt 80%, Rf 0.38 in (B).

The oil is employed without subsequent purification for the following steps. NMR correct.

EXAMPLE 56

N-(N-benzyloxy 3-carbamoyl 2-benzyl propanoyl)-glycine (Derivative 46)

0.5 g of the preceding compound are dissolved in 2 ml of TFA in the presence of 0.1 ml of anisole. The mixture is stirred at 0° C. for 30 mm, and then for 1 hour at room temperature. It is then evaporated to dryness under a vacuum. The oil obtained is triturated with 3×10 ml of dry ether. A gummy precipitate appears after with 5×10 ml of dry ether. The powder obtained is crystallized in EtOH. White crystals.

M.P. 176° C.; W 0.21 g; Rdt 51%; NMR correct; C,H,N.

EXAMPLE 57

N-(N-hydroxy 3-carbamoyl 2-benzyl propanoyl)-glycine (Derivative 47)

0.15 g of the preceding compound are hydrogenated at ordinary pressure under the conditions of Example 32. 0.11 g of a crystallized white solid is obtained.

M.P. 252° C.; Rdt 100%; Rf 0.61 in (A) NMR correct; C,H,N.

EXAMPLE 58

N-(N-benzyloxy 3-carbamoyl 2-benzyl propanoyl)-glycine benzylamide (Derivative 48)

1 g of 3-ethoxycarbonyl 2-benzyl propanoic acid is dissolved in a mixture of 30 ml of dry THF and 10 ml of anhydrous DMF. 1.2 g of glycine benzylamide trifluoroacetate are added without stirring. The coupling is effected under the conditions of Example 29. After the usual washings, 1.5 g of an oil which slowly crystallizes are obtained.

M.P. 62° C.; W 0.92 g; Rdt 76%; Rf 0.52 in (B) NMR correct; C,H,N.

EXAMPLE 59

N-(N-hydroxy 3-carbamoyl 2-benzyl propanoyl)-glycine benzylamide (Derivative 49)

0.3 g of the preceding compound are hydrogenated at ordinary pressure under the conditions of Example 32. 0.12 g of a white solid is obtained.

M.P. 207° C.; W 0.12; Rdt 50%; NMR correct; C,H,N.

EXAMPLE 60

(a) 2-(N-benzyloxy benzylcarboxamido) 3-phenyl propanoic acid 2 g of N-benzyloxy phenylalanine (KOLASKA, tetrahedron, 30, 3591–3595, 1974) are placed in a mixture of 10 ml of water and 10 ml of NaOH. 1.0 g of phenylacetyl chloride is added at 0° C. The mixture is extracted once with 20 ml of ether and then the aqueous phase is acidified to pH 2 with 2N HCl, and extracted with 3×10 ml of ether, dried and evaporated under a vacuum. 1.7 g of crystals are obtained.

M.P. 112° C.; Rdt 72%; Rf 0.42 (B); NMR correct; C,H,N.

(b) N-[2-(N-benzyloxy benzylcarboxamido) 3-phenyl propanoyl]-glycine benzyl ester (derivative 50)

1 g of the preceding comound is dissolved in 20 ml of dry THF. A mixture in 10 ml of THF and 10 ml of CHCl₃ of 0.87 g of glycine benzyl ester tosylate and 0.27 g of triethylamine is added. After stirring for 5 mn at 0° C., there are added in succession at 0° C. 1 ml of HOBT, H₂O and 1 ml of DCC under the conditions of the peptidic coupling (Example 29). After 12 hours the usual treatment is effected. 1.3 g of a colourless oil purified by chromatography on a silica column (CHCl₃/CH₃OH, 80/20) are obtained.

Rdt 91%; Rf 0.65 in the same solvent. NMR correct; C,H,N.

EXAMPLE 61

N-[2-(N-hydroxy benzylcarboxamido) 3-phenyl propanoyl]glycine (derivative 51)

1 g of the preceding compound is hydrogenated at ordinary pressure as in Example 32. 0.42 g of white crystals (EtOH) is obtained.

Rdt 62%; M.P. 125° C.; Rf 0.34 in (B) NMR correct; C,H,N.

EXAMPLE 62

(a) 2-(N-benzyloxy β-trifluoroethyl carboxamido)-3-phenyl propanoic acid 2 g of N-benzyloxy phenylalanine are treated as in Example 60a with 1.10 g of trifluoromethyl acetic acid chloride. 1.5 g of oil which slowly crystallizes are obtained.

M.P. 82° C.; Rdt 53%; Rf 0.21 in (B); NMR correct; C,H,N.

(b) N-2-[(N-benzyloxy β-trifluoroethyl caboxamido) 3-phenyl propanoyl]-glycine benzyl ester (Derivative 52)

1 g of the preceding compound is coupled under the conditions of the peptide coupling (Example 29) with 0.9 g of glycine benzyl ester tosylate. After the usual treatments, 1.1 g of a pasty solid are obtained which solid is used without prior purification for the following experiment.

Rf 0.42 in (B).

EXAMPLE 63

N-[2-N-hydroxy β-trifluoroethyl carboxamido) 3-phenyl propanoyl]-glycine (Derivative 53)

0.5 g of the preceding compound is hydrogenated under the usual conditions (Example 32). 0.25 g of a white solid is obtained.

M.P. 208° C.; Rdt 83%; Rf 0.64 in (A).

EXAMPLE 64

N-[2-(N-benzyloxy N-p.fluorobenzyl carbamoyl) 3-phenyl propanoyl]-glycine benzyl ester (Derivative 54)

0.5 of the compound 35b is dissolved in 30 ml of dry THF. An equivalent (0.084 g) of freshly prepared of sodium ethylate if added. The mixture is stirred for 10 hours at room temperature under a nitrogeneous current, and then there is slowly added 0.14 g of p.fluorobenzyl chloride and the mixture is allowed to stand for 10 hours at room temperature and then refluxed for 2 hours. The material is concentrated to dryness, taken up with AcOEt, washed with water, dried, evaporated under a vacuum. 0.12 g of a colourless oil is obtained which is purified by passage on a silica gel column (eluent CHCl₃/Et₂O, 50/50).

Rf 0.75 in (B).

EXAMPLE 65

N-[2-(N-hydroxy N-p.fluorobenzyl carbamoyl) 3-phenyl propanoyl]-glycine (Derivative 55)

0.08 g of the preceding compound is hydrogenated at ordinary pressure as in Example 32. 0.035 g of a white solid is obtained.

M.P. 164° C.; Rf 0.12 in (A); NMYR correct; C,H,N.

EXAMPLE 66

N-[N-benzyloxy N-p.fluorobenzyl 3-carbamoyl 2-benzyl propanoyl]-glycine tertiobutylic ester (Derivative 56)

0.5 g of the compound 55 is treated as in Example 64 with p.fluorobenzyl chloride. After treatment, there is obtained 0.42 g of an oil (Rf=0.55 in (B)) employed without subsequent purification for preparing the compound 74.

EXAMPLE 67

N-[3-(N-benzyloxy N-p.fluorobenzyl carbamoyl) 2-benzyl propanoyl]-glycine (Derivative 57)

0.42 of the preceding compound is dissolved in 1 ml of TFA at 0° C. The solution is left to stand without stirring for 30 mn, and evaporated under a vacuum. The residual oil is washed with 10×10 ml of dry ether to a neutral ph. A hygroscopic white powder is obtained. Rf 0.75 in (B); W 0.30 g; Rdt 80%; NMR correct.

EXAMPLE 68

N-[3-(N-hydroxy N-p.fluorobenzyl carbamoyl) 2-benzyl propanoyl]-glycine (Derivative 58)

0.3 g of the preceding compound is hydrogenated as in Example 32. 0.15 g of a crystallized solid is obtained.
M.P. 212° C.; Rdt 62%; NMR correct; C,H,N.

EXAMPLE 69

(a) 3-(N-benzyloxy p.fluorobenzylcarboxamido) 2-benzyl propanoic acid 5 g of the compound 43a are condensed with 3.05 ml of p.fluorophenyl acetyl chloride as in Example 60. After the usual treatment 3.8 g of pale yellow crystals are obtained.
M.P. 96° C.; Rdt 51%; NMR correct; C,H,N.

(b) N-[3-(N-benzyloxy p.fluorobenzylcarboxamido) 2-benzyl propanoyl]-glycine (Derivative 59)

3 g of the preceding compound are condensed as in Example 29 with 2.32 g of glycine benzyl ester tosylate. 3.52 g of oil are obtained, which oil is employed without purification for preparing the compound 70.

EXAMPLE 70

N-[3-(N-hydroxy p.fluorobenzylcarboxamido) 2-benzyl propanoyl]-glycine (Derivative 60)

3 g of the compound 69b are hydrogenated at ordinary pressure under the conditions of Example 32. After crystallization in EtOH, 1.10 g of a white solid are obtained.
M.P. 174° C.; Rdt 54%; Rf 0.32 in (A); NMR correct; C,H,N.

EXAMPLE 71

(a) 3-(N-benzyloxy β-trifluoroethylcarboxamido) 2-benzyl propanoic acid 3 g of the compound 43a are condensed with 1.54 g of trifluoromethyl acetic acid chloride as in Example 60. 3.12 g of yellow crystals are obtained.
M.P. 64° C.; Rdt 76%; Rf 0.45 in (B); NMR correct; C,H,N.

(b) N-[3-(N-benzyloxy trifluoromethyl acetamido) 2-benzyl propanoyl]-glycine benzyl ester (Derivative 61)

2 g of the preceding compound are condensed as in Example 29 with 1.7 g of glycine benzyl ester tosylate. There are obtained 1.62 g of a yellow oil which is employed without subsequent purification for the preparation of compound 72.

EXAMPLE 72

N-[3-(N-hydroxy trifluoromethyl acetamido) 2-benzyl propanoyl]-glycine (Derivative 62)

1 g of the compound 71 is hydrogenated at ordinary pressure under the conditions of Example 32. After crystallization in AcOEt, 0.62 g of a pale yellow solid is obtained.
M.P. 131° C.; Rdt 92%; Rf 0.44 in (A) NMR correct; C,H,N.

EXAMPLE 73

N-(N-hydroxy 3-formamido 2-benzyl propanoyl)-glycine p-fluoro benzylamide (Derivative 63)

0.6 g of the compound 45b is reacted under the conditions of the peptidic coupling (Example 29) with 0.4 g of glycine para-fluoro benzyl amide. After the usual treatments, 0.46 g of an oil is obtained.
Rdt 50%; Rf 0.72 in CHCl$_3$/CH$_3$OH, 5/1.

The compound is then hydrogenated at ordinary pressure as in Example 32. 360 mg (Rdt 95%) of a white solid are obtained.
M.P. 175° C.; Rf 0.53 in CHCl$_3$/CH$_3$OH, R/1 NMR correct; C,H,N.

EXAMPLE 74

N-(N-hydroxy 3-formamido 2-benzyl propanoyl)-tryptophane p-fluoro benzylamide (Derivative 64)

0.6 g of the compound 45b is reacted under the conditions of the peptidic coupling (Example 29) with 0.6 g of tryptophane para-fluoro benzyl amide. After the usual treatments, 0.54 g of an oil is obtained.
Rdt 50%; Rf 0.7 in CHCl$_3$/CH$_3$/OH, R/1.

0.50 g of this compound are employed without subsequent purification for a hydrogenation at ordinary pressure, as in Example 32. 395 mg of a white solid are obtained.
Rdt 95%; Rf 0.52 in ChCl$_3$/CH$_3$OH, R/1; NMR correct; C,H,N.

EXAMPLE 75

N-(N-hydroxy 3-formamido 2-benzyl propanoyl)-alanine p-fluoro benzylamide (Derivative 65)

0.600 g of the compound 45b are reacted under the conditions of the peptidic coupling (Example 29) with 0.20 g of alanine p-fluoro benzyl amide. After the usual treatments 0.38 g of an oil is obtained.
RDT 55%; Rf 0.79 in CHCl$_3$/CH$_3$OH, 5/1.

0.35 g of this compound are employed without subsequent purification for hydrogenation at ordinary pressure, as in Example 32. 220 mg of a white solid are obtained.
RF 0.58 in CHCl$_3$/CH$_3$OH, R/1; NMR correct; C,H,N.

EXAMPLE 76

[2-(N-hydroxy carbamoyl) 3-phenyl propanoyl]-leucine p-fluoro benzylamide (Derivative 66)

0.600 g of the compound 35a are coupled with 0.50 g of leucine p-fluoro benzyl amide under the conditions of Example 34. After treatment, 730 mg of an amorphous white solid (Rdt 75%) are obtained.

0.700 g of this compound is hydrogenated under the conditions of Example 32. 520 mg of an unstable white solid compound are obtained.

Rdt 90%; M.P. 175° C.; Rf 0.48.

EXAMPLE 77

N-(N-hydroxy 2-formamido 3-pentafluorophenyl propanoyl)glycine butyl ester (Derivative 67)

9 g of pentafluorobenzaldehyde are condensed on 7 g of diethyl malonate in accordance with the process described in Organic Synthesis vol. III, page 377. 10 g (69%) of diethyl pentafluorobenzylmalonate are obtained which is hydrogenated at ordinary pressure in the presence of palladium on charcoal into diethyl pentafluorobenzylmalonate (92%).

By adopting the process described in the patent FR 8 008 601 for preparing the benzylacrylic acid, the pentafluorobenzyl acrylic acid is obtained. The latter compound gives by means of the processes described in Examples 45 and 46 3-(benzyloxyformamido 2-pentafluorobenzyl propanoic acid. By condensing the latter compound with glycine butyl ester in accordance with the process of Example 49 and catalytic hydrogenation under the conditions of Example 32, the derivative 77 is obtained.

White solid-RF 0.53, CHCl$_3$/CH$_3$OH, R/1; M.P. 55° C. NMR correct; C,H,N.

EXAMPLE 78

(a) N-benzyloxy 2-formamido 1-benzyl ethylamine 1 g of the compound 43b is treated in accordance with the process of Ninomiya et al (Chem. Pharm. Bull. 22, 1398 (1974) with diphenylphosphorazide in benzene in the presence of triethylamine, then with tertiobutyl alcohol so as to give 610 mg (50%) of a pale yellow oily compound.

The oil is treated with trifluoroacetic acid and yields 540 mg of trifluoroacetate of 78a (85%). White solid.
M.P. 125° C.; Rf 4/1/1 0.42.

(b) [N-formyl N-benzyloxy N'(2)benzyloxycarbonyl) acetyl]1,2-diamino 2-benzyl ethane (Derivative 68)

500 mg of trifluoroacetate 78a are coupled with 245 mg of malonic acid monobenzylester in the presence of DCC/HOBT in accordance with the conventional process of peptidic coupling (Example 43c). After successive washings, 500 mg of a thick colourless oil are obtained.

Rdt 90%; Rf 0.55 in CHCl$_3$/MeOH, 5.1.

EXAMPLE 79

[N-formyl N-hydroxy N'(2-carboxy) acetyl]1,2-diamino 2-benzyl ethane (Derivative 69)

300 mg of preceding compound are hydrogenated at ordinary pressure under the conditions of Example 32. 160 mg of a white solid are obtained.

M.P. 182° C. (90%); Rf. 0.20 in ChCl$_3$/MeOH/acetic acid, 9/1/0.5.

EXAMPLE 80

[N-formyl β-benzyloxy N'(2-benzylcarboxamido) acetyl]1,2-diamino 2-benzyl ethane (Derivative 70)

500 mg of trifluoroacetate of 78a are coupled with 245 mg of malonic acid monobenzylamide in the presence of DCC/HOBT in accordance with the process of Example 43c.

After successive washings, 510 mg of a thick colourless oil which slowly crystallizes are obtained.

Rdt 91%; Rf 0.40 in CHCl$_3$/MeOH/acetic acid 9/1/0.5.

EXAMPLE 81

[N-formyl N-hydroxy N'(2-benzylcarboxamido) acetyl]1,2-diamino 2-benzyl ethane (Derivative 71) 300 mg of the preceding compound are hydrogenated at ordinary pressure under the conditions of Example 32.

215 mg of a white solid (90%) are obtained.

M.P. 145° C.; Rf 0.30 in CHCl$_3$/MeOH/acetic acid 9/1/0.5.

The pale yellow oil obtained crystallizes in plates.
M.P. 101°-108° C.; W 1.6 g; Rf 0.40 in CHCl$_3$/MeOH, 7/3; C,H,N.

(b) 3-(N-benzyloxy formamido) 2-(β-indolylmethyl) propanoic acid

1/ Preparation of 3-benzyloxyamino 2-β-indolylmethyl propanoic acid.

There is added to room temperature a solution of 1.12 g (0.009 mole) of 0. benzyl hydroxylamine in solution in 20 ml of CH$_3$OH, to 1.5 g (0.008 mole) of the compound of Example 82a-2 dissolved in 20 ml of CH$_3$OH. The mixture is refluxed for 5 hours. The treatment is then as in Example 43. The oil obtained crystallizes.

M.P. 67° C.; W 1.4 g; Rf 0.23 in CHCl$_3$/MeOH, 9/1 NMR correct

2/ 1.3 g of the preceding compound are added to 17 ml of HCO$_2$H and then the mixture is treated and extracted under the conditons of Example 35. A thick oil which does not crystallize is obtained.

Rf 0.4 in CHCl$_3$/CH$_3$OH, 9/1; W 0.7 g. The NMR being correct, the product is employed without purification for the following reactions.

(c) N-[3-(N-benzyloxy formamido 2-β-indolylmethyl propanoyl] glycine benzyl ester (Derivative 72)

0.5 g of the compound obtained in step (b) in solution in 50 ml of dry THF are coupled with 0.4 g of glycine benzyl ester tosylate in accordance with the Example 43c.

EXAMPLE 82

(a) 2-methylene 3-β-indolyl propanoic acid

1/2.61 g (0.01 mole) of 2-carboxy 3-β-indolyl propanoic acid ethyl ester obtained by the monosponification of β-indolylmethyl malonic acid, itself obtained by the action of 2-chloromethyl indole on diethyl malonate according to Organic Synthesis, vol. 2, pp. 279, are stirred at room temperature for 24 hours in accordance with Mannick (Ber 57, 1116 (1924) with 2.23 g of 30% formol and 0.73 g of diethylamine. 5 ml of water are added and the organic phases are extracted with 3×50 ml of ether. The organic phases are washed in succession with 20 ml of 0.5N HCl, then with 20 ml of water and finally with 20 ml of NaCl saturated solution. The product is dried on Na$_2$SO$_4$ and concentrated to dryness.

A pale yellow oil which crystallizes slowly is obtained.

M.P. 40°–60° C.; W 2.10 g; Rf 0.89 in CHCl$_3$/EtOH (9/1); NMR correct.

2/2 g of the preceding ester are dissolved in 20 ml of ethanol and stirred with 1.2 equivalent of 1N NaOH solution for 20 hours at room temperature. The product is evaporated to dryness and taken up with 20 ml of water, and extracted once with ether. The aqueous phase is acidified to pH 2 with 2N HCl. The material is extracted with 2×50 ml of ether, washed with water, dried on Na$_2$SO$_4$ and evaporated to dryness.

After the usual successive treatments, 0.66 g of a brown oil is obtained.

Rf 0.57 in CHCl$_3$/MeOH, 9/1. NMR correct.

EXAMPLE 83

N-[3-(N-hydroxy-formamido)-2-β-indolylmethyl propanoyl]glycine (Derivative 73)

0.55 g of the compound 82 is hydrogenated at ordinary pressure under the conditions of Example 32. 0.42 g of a white solid is obtained.

M.P. 228° C.; Rf 0.38 in (A).

EXAMPLE 84

N-[3-(N-benzyloxy formamido)2-isobutyl propanoyl]glycine benzyl ester (Derivative 74)

(a) 3.12 g (0.017 mole) of the isobutyl malonate ethyl monoester obtained by the action of isobutyl chloride on diethyl malonate followed by a monosaponification, are stirred for 24 hours at room temperature with 1.5 g of 30% formol and 1.24 g of diethylamine. After treatment as in Example 82a-1, 2.8 g of an oil are obtained.

Rf 0.92 in CHCl$_3$/MeOH, 9/1; NMR correct.

The oil is employed crude for the followins step.

(b) 2.5 g of the preceding ester are dissolved in 20 ml of ethanol and saponified according to the conditions of Example 82a-2. 1.8 g of a pale yellow solid are obtained.

M.P. 65° C.; MNR correct, C,H,N corresponds to 2-isobutyl acrylic acid.

(c) 1.5 g of 2-isobutyl acrylic acid are condensed with O.benzylhydroxylamine in accordance with Example 82b-1. The oil obtained has a correct NMR spectrum.

W 1.6 g; Rf 0.18 in CHCl$_3$/MeOH.

(d) 1.5 g of the preceding oil are added to 16 ml of HCO$_2$H and the mixture is treated as in Example 35. The oil obtained has a correct NMR spectrum and is employed for the following peptidic condensation.

W 1.35 g; Rf 0.31 in CHCl$_3$/MeOH.

(e) 1.07 g of the preceding compound are coupled in solution in THF with 1.20 g of glycine benzyl ester tosylate, and then the mixture is treated as in Example 43c. 1.84 g of the compound 84 are obtained. The pale yellow oil is obtained pure by chromatography on a silica gel column with the use of the mixture CHCl$_3$/MeOH, 8/2, as eluent.

NMR correct; C, H,N; RF 0.34 in CHCl$_3$/MeOH, 9/1.

EXAMPLE 85

N-[3-(N-hydroxy formamido)2-isobutyl propanoyl]-glycine (Derivative 75)

1.2 g of the preceding compound are hydrogenated at ordinary pressure under the conditions of Example 32 which gives 0.62 g of a white solid.

M.P. 164°–170° C.; NMR correct; C,H,N.

EXAMPLE 86

(a) 2-N-benzyloxycarbamoyl 3-isopropyl propanoic acid 2 g (0.0106 mole) of isobutylmalonate ethyl monoester prepared according to Example 84a are coupled with 1.30 g O-benzylhydroxylamine base under the conditions of the peptidic synthesis (Example 29). After the usual treatment, a colourless oil is obtained which is saponified with 1N NaOH at 5° C. for 5 hours in ethanol. After acidification, extraction with ether and evaporation to dryness a white solid is obtained.

W 2.1. g; M.P. 161° C. (EtOH); NMR correct; C,H,N.

(b) N-[2-(N-benzyloxycarbamoyl 3-isopropyl propanoyl]glycine benzyl ester (Derivative 76)

1.5 g of the preceding compound are coupled with 2.2 g of glycine benzyl ester tosylate according to the conditions of Example 33b. After treatment, 1.2 g of a pale yellow solid are obtained.

M.P. 50°–60° C.; NMR correct; C,H,N

EXAMPLE 87

N-[2-(N-hydroxycarbamoyl)3-isopropyl propanoyl]glycine (Derivative 77)

1 g of the preceding compound is hydrogenated at oridinary pressure as in Example 32. 527 mg of a white solid are obtained.

M.P. 147°–151° C. (H$_2$O); Rf 0.38 in (A); NMR correct; C,H,N.

EXAMPLE 88

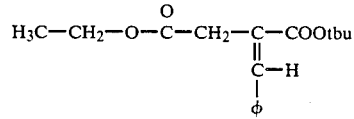

α-tertiobutyl β-ethyl benzalsuccinate 5 g of β-ethyl-α-benzalsuccinate are dissolved in 20 ml of isobutylene. After stirring for 24 hours at room temperature, ether is added to the mixture. The organic solution is washed with 4% bicarbonate and water, then dried on Na$_2$SO$_4$ and exposed to dryness, which gives 4.96 g of an oil.

Rdt 80%; NMR correct; C,H,N; Rf 0.9 in CHCl$_3$/CH$_3$OH 9/1.

EXAMPLE 89

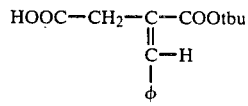

α-benzalsuccinic acid monoterbutylate 4.5 g of the preceding compound are dissovled in 50 ml of ethanol. The solution is cooled to 0° C. and 34 ml of N sodium hydroxide. After stirring for 1 hour at 0° C. and one night at room temperature, the mixture is evaporated under a vacuum and the residue is taken up with 30 ml of water. The pH is brought to 1 by the addition of 2n HCl and the product is extracted with ether. The organic solution is washed with water, dried on Na$_2$SO$_4$ and evaporated under a vacuum. 4.07 g of cream-colored crystals are obtained.

Rdt 80%; M.P. 114° C.; Rf 0.51 in CHCl$_3$/CH$_3$OH 9/1 NMR correct; C,H,N.

$$\bigcirc\!\!-\!CH_2\!-\!O\!-\!NH\!-\!CO\!-\!CH_2\!-\!\underset{\underset{\phi}{\overset{|}{C\!-\!H}}}{\overset{\|}{C}}\!-\!COOtbu$$

4 g of the preceding compound are reacted under the peptidic coupling conditions with 2.43 g of benzylhydroxylamine hydrochloride. After the usual treatments, 5.49 g of a thick oil are obtained.

Rdt 98%; Rf 0.52 in CHCl$_3$/CH$_3$OH 9/1 NMR correct; C,H,N.

EXAMPLE 91

$$\bigcirc\!\!-\!CH_2\!-\!O\!-\!NH\!-\!CO\!-\!CH_2\!-\!\underset{\underset{\phi}{\overset{|}{C\!-\!H}}}{\overset{\|}{C}}\!-\!COOH$$

5 g of the preceding compound are stirred at 0° C. in the presence of 14 ml of TFA for 3 hours. The product is evaporated under a vacuum. The oil obtained is triturated a plurality of times with dry ether, which gives 3.4 g of a gummy solid.

Rdt 80%, Rf 0.8 in butanol/acetic acid/water 4.1.1. NMR correct; C,H,N.

EXAMPLE 92

$$\bigcirc\!\!-\!CH_2\!-\!O\!-\!NH\!-\!CO\!-\!CH_2\!-\!\underset{\underset{\phi}{\overset{|}{C\!-\!H}}}{\overset{\|}{C}}\!-\!CO\!-\!NH\!-\!glyOMe$$

Derivative 78

3.3 g of the preceding compound are put in the presence of 1.33 g of glycine methyl ester hydrochloride under the peptidic coupling conditions. After the usual treatments, 3.53 g of a white powder are obtained.

Rdt 87%; W 102° C.; Rf 0.65 in CHCl$_3$/CH$_3$OH 9/1 NMR correct; C,H,N.

EXAMPLE 93

$$\bigcirc\!\!-\!CH_2\!-\!O\!-\!NH\!-\!CO\!-\!CH_2\!-\!\underset{\underset{\phi}{\overset{|}{C\!-\!H}}}{\overset{\|}{C}}\!-\!CO\!-\!NH\!-\!glyOH$$

Derivative 79

3.5 g of the preceding compound are dissolved in 30 ml of 3/1 mixture of methanol and water. 11 ml of N sodium hydroxide are added to the solution cooled to 0° C. After stirring for 1 hour at 0° C. and for 3 hours at room temperature, the pH is brought to 1 with N HCl. The product is extracted with ether. The organic solution is washed with water, dried on Na$_2$SO$_4$ and evaporated under a vacuum. The power obtained is crystallized in ether to give 8.75 g of white crystals.

Rdt 82%; M.P. 171° L C.; Rf 0.83 in butanol acetic acid/water 4.1.1. NMR correct; C,H,N.

EXAMPLE 94

$$H\!-\!\overset{\overset{OH}{|}}{N}\!-\!\overset{\overset{O}{\|}}{C}\!-\!CH_2\!-\!\underset{\underset{\phi}{\overset{|}{CH_2}}}{\overset{|}{CH}}\!-\!CO\!-\!NH\!-\!glyOH$$

Derivative 80

0.35 g of the preceding compound are dissolved in methanol and stirred at ordinary pressure in the presence of palladium on charcoal for 3 hours. After having filtered the catalyst, the solvent is evaporated under a vacuum to give 0.24 g of a thick oil.

Rdt 90%; Rf 0.54 in butanol/acetic acid/water 4.1.1. NMR correct; C,H,N.

EXAMPLE 95

$$\bigcirc\!\!-\!CH_2O\!-\!NH\!-\!CO\!-\!CH_2\!-\!\underset{\underset{\phi}{\overset{|}{C\!-\!H}}}{\overset{\|}{C}}\!-\!CO\!-\!NH\!-\!CH_2\!-\!CO\!-\!O\!-\!(CH_2)_2N\!\!\begin{array}{c}CH_3\\ \\CH_3\end{array}$$

300 mg of the compound of Example 93 are put in the presence of 72 mg of 2-dimethylamino-ethane under the peptidic coupling conditions. After the usual treatments, 317 mg of an oil are obtained.

Rf 0.55 in CHCl$_3$/CH$_3$OH 9/1. Rdt 89%; NMR correct; C,H,N.

EXAMPLE 96

$$HN\!-\!CO\!-\!CH_2\!-\!\underset{\underset{\phi}{\overset{|}{CH_2}}}{\overset{|}{CH}}\!-\!CO\!-\!NH\!-\!CH_2\!-\!\overset{\overset{O}{\|}}{C}\!-\!O\!-\!(CH_2)_2\!-\!N\!\!\begin{array}{c}CH_3\\ \\CH_3\end{array}$$
(with OH on HN)

Derivative 82

310 mg of the preceding compound are hydrogenated under the conditions of the compound 7 so as to give a pasty solid which crystallizes in methanol in the form of white crystals.

W 192 mg; Rdt 80%; Rf 0.42 in CHCl$_3$/CH$_3$OH/CH$_3$COOH 9/1.0.5—NMR correct; C,H,N.

EXAMPLE 83

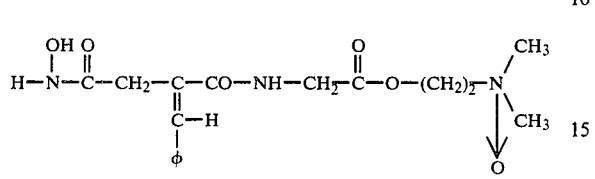

Derivative 83

100 mg of the preceding compound are dissolved in 0.5 ml of acetonitrile. There is added to the solution 0.05 ml of an aqueous solution of 30% of H$_2$O$_2$ at 0° C. After stirring for 24 hours at room temperature, 10 ml of butanol and a 5% aqueous solution of NaCl are added. The organic solution is washed with water, and then evaporated under a vacuum to give 84 mg of a thick oil.

Rdt 80%; Rf 0.13 in butanol/acetic acid/water 4/1/1. NMR correct; C,H,N.

EXAMPLE 98

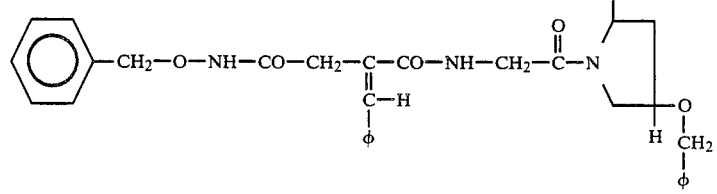

Derivative 84

0.5 g of the compound are put in the presence of 368 mg of benzyl-hydroxyproline methyl ester hydrochloride under the peptidic coupling conditions. After the usual treatments, 515 mg of an oil are obtained.

Rdt 90%; RF 0.33 in CHCl$_3$/H$_3$COH 9/1; NMR correct; C,H,N.

EXAMPLE 99

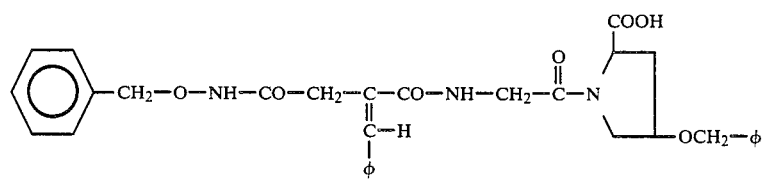

Derivative 85

500 mg of the preceding compound are saponified under the conditions of the compound n° 6 so as to give 405 mg of a foam.

Rdt 83%; Rf 0.53 in CHCl$_3$/CH$_3$OH 7/3; NMR correct; C,H,N.

EXAMPLE 100

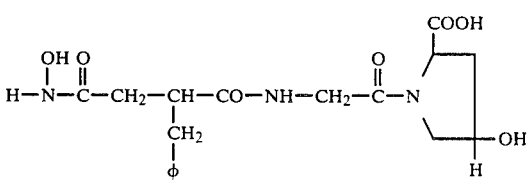

Derivative 86

400 mg of the preceding compound are hydrogenated under the conditions of the compound of Example 94 to give 252 mg of a resinous product.

Rdt 92%, Rf 0.31 in CHCl$_3$/CH$_3$OH/CH$_3$COOH 9/1/0.5 NMR correct; C,H,N.

EXAMPLE 101

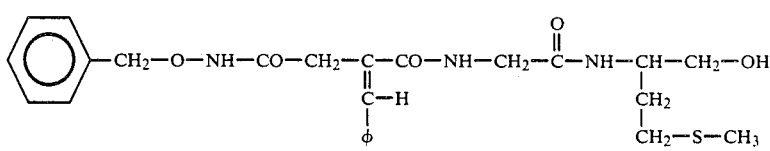

Derivative 87

350 mg of the compound of Example 93 are combined with 128 mg of methionilol under the conditions of peptidic coupling to give 401 mg of an oil.

Rdt 87%; Rf 0.28 in CHCl$_3$/CH$_3$OH 7/3; NMR correct; C,H,N.

EXAMPLE 102

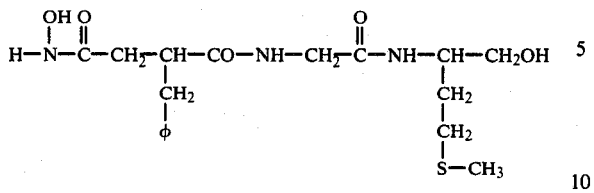

Derivative 88

350 mg of the preceding compound are hydrogenated under the conditions of the compound of Example 94 to give 257 mg of an oil.

Rdt 90%; Rf 0.30 in butanol/acetic acid/water 4/1/1. NMR correct C,H,N.

EXAMPLE 103

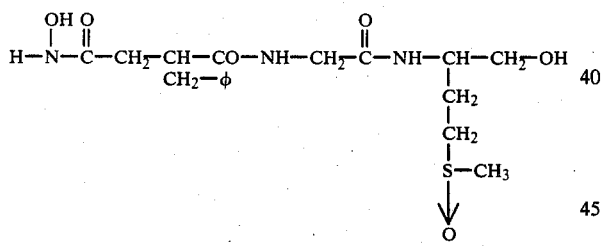

Derivative 89

150 mg of the preceding compound are treated under the conditions of the compound of Example 96 to give 156 mg of a thick oil.

Rdt 75%; Rf 0.20 in CHCl$_3$/CH$_3$OH 7/3. NMR correct; C,H,N.

EXAMPLE 104

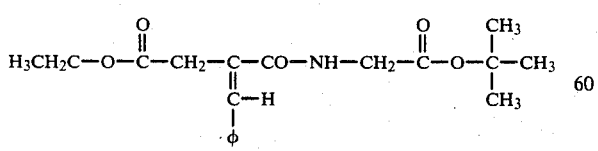

1 g of β-ethyl α-benzalsuccinate is combined with 715 mg of glycine methyl ester hydrochloride under peptidic coupling conditions to give 1.48 g of an oil.

Rdt 100%; Rf 0.82 in CHCl$_3$/CH$_3$OH 9/1; NMR correct; C,H,N.

EXAMPLE 105

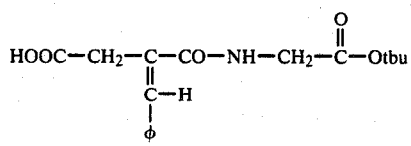

1.4 g of the preceding compound are subjected to an alkaline hydrolysis under the conditions of the compound of Example 93 to give 1.06 g of a thick oil.

Rdt 83%; Rf 0.77 in butanol/acetic acid/eau 4/1/1. NMR correct; C,H,N.

EXAMPLE 106

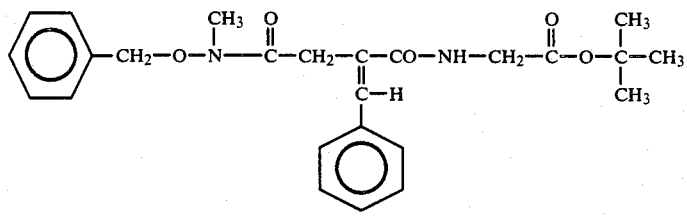

Derivative 90

1 g of the preceding compound is combined with 802 mg of N-methylobenzylhydroxylamine trifluoroacetate under the peptidic coupling conditions to give an oil which, in crystallizing, yields 984 mg of white crystals.

Rdt 70%; M.P. 125° C.; Rf 0.69 in CHCl$_3$/CH$_3$OH 9/1; NMR correct; C,H,N.

EXAMPLE 107

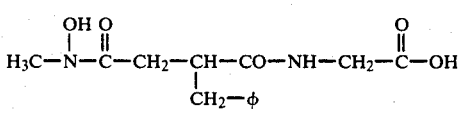

Derivative 91

900 mg of the preceding compound are dissolved under the conditions of the compound of Example 94 to give 651 mg of an oily product.

Rdt 91%; Rf 0.59 in CHCl$_3$/CH$_3$OH 9/1; NMR correct; C,H,N.

EXAMPLE 108

$$H_3C-N(OH)-C(O)-CH_2-CH(CH_2-\phi)-CO-NH-CH_2-C(O)-OH$$

Derivative 92

600 mg of the preceding compound are hydrolyzed under the conditions of the compound of Example 91 to give 393 mg of a thick oil.

Rdt 98%; Rf 0.22 in CHCl$_3$/CH$_3$OH/CH$_3$COOH 9/1/0.5 NMR correct; C,H,N.

EXAMPLE 109

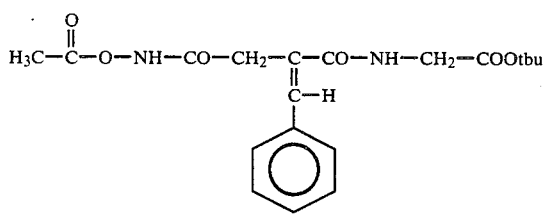

Derivative 93

500 mg of the compound of Example 104 are combined with 117 mg of o-acetyl-hydroxylamine under the peptidic coupling conditions to give 526 mg of a thick oil.

Rdt 89%; Rf 0.65 in CHCl$_3$.CH$_3$OH 9/1; NMR correct; C,H,N.

EXAMPLE 110

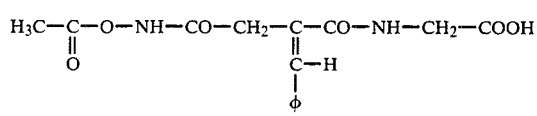

Derivative 94

500 mg of the preceding compound are hydrolyzed under the conditions of the compound no 4 to give 332 mg of pasty product.

Rdt 78%; Rf 0.63 in butanol/acetic acid/water 4/1/1. NMR correct; C,H,N.

EXAMPLE 111

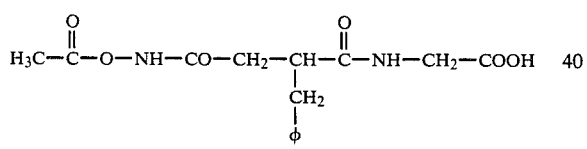

Derivative 95

300 mg of the preceding compound are hydrogenated under the conditions of compound no 7, which gives 280 mg of an oily product.

Rdt 93%; Rf 0.60 in butanol/acetic acid/water 4/1/1; NMR correct; C,H,N.

EXAMPLE 112

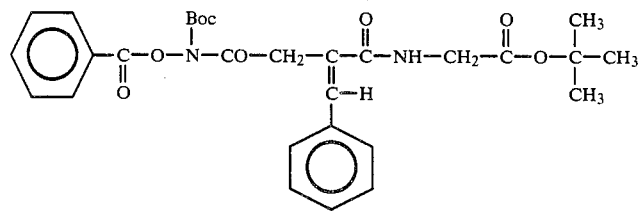

500 mg of the compound of Example 104 are combined with 190 mg of o-benzyl-hydroxylamine under the conditions of peptidic coupling, which gives 564 mg of a thick oil.

Rdt 85%; Rf 0.54 in CHCl$_3$/CH$_3$OH 9/1. NMR correct; C,H,N.

EXAMPLE 113

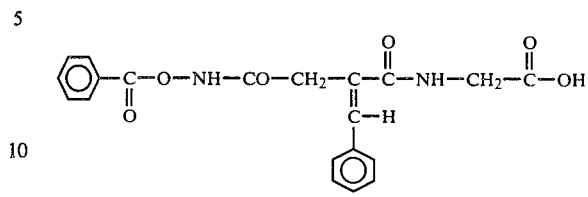

Derivative 96

500 mg of the preceding compound are treated with trifluoroacetic acid under the conditions of compound no. 4 to give 349 mg of a foamy product.

Rdt 77%; Rf 0.6 in butanol/acetic acid/water 4/1/1. NMR correct; C,H,N.

EXAMPLE 114

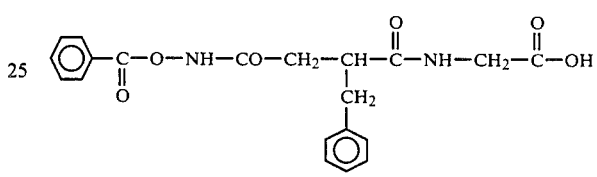

Derivative 97

300 mg of the preceding compound are hydrogenated under the conditions of the compound no. 94 to give 268 mg of an oily product.

Rdt 89%; Rf 0.55 in butanol/acetic acid/eau 4/1/1.

EXAMPLE 115

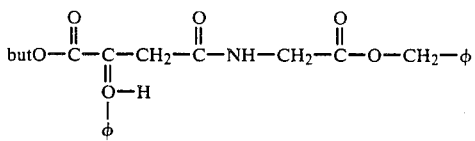

366 mg of the compound of Example 89 are combined with 471 mg of glycine methyl ester paratoxylate under the peptidic coupling conditions, which gives 570 mg of a fluid oil.

Rdt 100%; Rf 0.83 in CHCl$_3$/CH$_3$OH 9/1; NMR correct; C,H,N.

EXAMPLE 116

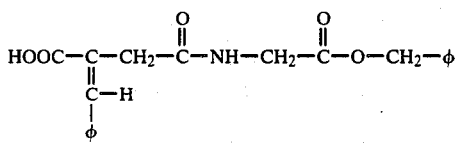

500 mg of the preceding compound are treated with trifluoroacetic acid under the conditions of the compound of Example 91 to give 302 mg of a white powder.

M.P. 145° C.; Rdt 70%; Rf 0.16 in CHCl$_3$/CH$_3$OH 9/1 NMR correct; C,H,N.

EXAMPLE 117

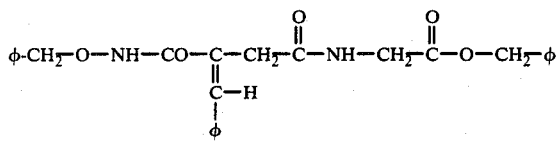

Derivative 98

300 mg of the preceding compound are combined with 150 mg of o-benzyl-hydroxylamine hydrochloride under the peptidic coupling conditions to give 81 mg of white crystals.

M.P. 151° C.; Rdt 60%; Rf 0.5 in CHCl$_3$/CH$_3$OH 9/1 NMR correct; C,H,N.

EXAMPLE 118

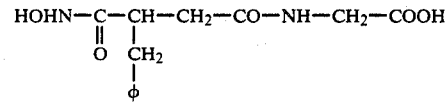

78 mg of the preceding compound are hydrogenated under the conditions of the compound of Example 94 to give 46 mg of a white product.

M.P. 129° C.; Rdt 97%; Rf 0.38 in butanol/acetic acid/water 4/1/1. NMR correct; C,H,N.

EXAMPLE 119

N-(N-benzyloxy-8-carbamoyl-2-benzylidene)glycine piperidino ethyl ester.

Derivative 100

3 g of the compound of Example 91 are combined with 2.5 g of glycine piperidino ethyl ester trifluoroacetate under the conditions of peptidic synthesis. After the usual treatments, 3.5 g of a white powder are obtained.

M.P. 106° C.; Rdt 65%; Rf 0.62 in CHCl$_3$/CH$_3$OH 9/1 NMR correct; C,H,N.

EXAMPLE 120

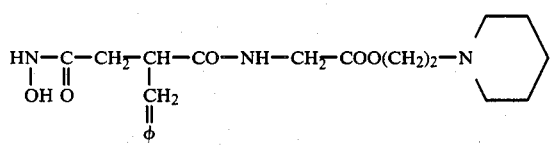

N-(N-3-hydroxycarbamoyl-2-benzyl-propanoyl)glycine piperidino ethyl ester.

Derivative 101

1 g of the preceding compound is hydrogenated at ordinary pressure under the conditions of Example 32. 0.76 g of a crystallized white solid is obtained.

M.P. 231° C.; Rdt 100%; Rf 0.7 in (A); NMR correct; C,H,N.

The results of the biological and pharmacological studies reported below show the interesting enkephalinase-inhibiting, antalgic, antidepressive, antidiarrhea and hypotensive properties of the derivatives of formula I.

Consequently, an object of the present invention is to provide a pharmaceutical composition having in particular enkephalinase-inhibiting, antalgic, antidepressive, andidiarrhe and hypotensive properties, said composition comprising, as an active ingredient, a compound of formula I or an addition salt with a pharmaceutically acceptable acid or base of said compound.

A-Biological study (I) Dosage of the "enkephalinasic" activity (enkephalin dipeptidylcarboxypeptidasic) and determination of the effect of the inhibitors.

The enzyme preparation employed is a membrane fraction from the striatum of the rat or mouse.

This fraction is obtained by homogenization at 4° C. in 20 volumes of Tris-Hl buffer 0.05M (pH 7.4) followed by two successive centrifugations (1000 g×min. and 200,000 g×min.) at the end of which the sediment of the second centrifugation is retained. It is washed by resuspension in 10 ml of the buffer followed by centrifugation (200,000 g×min.) and the resulting sediment is in turn washed superficially to complete the removal soluble enzymes. The resulting membrane fraction is taken up into the buffer at 4° C. to obtain a suspension comprising about 1.5 mg of proteins per ml.

An aliquot sample (50 μl) of the membrane suspension is then incubated in a final volume of 100 μl at 25° C. in the presence of 10 nM leucine-enkephalin $^3$H (39 Ci/mmole), previously purified by column chromatography over Porapak Q (100–120 mesh, Waters Assoc.) and 0.1 mM puromycine, an aminopeptidase inhibitor. The incubation time is generally set at 15 min. so as to determine the initial rate of formation of tripeptide Try-Gly-Gly-$^3$H caracteristic of the enkephalin dipeptidylcarboxypeptidasic (enkephalinasic) activity. The reaction is terminated by the addition of 25 μl of 0.2N HCl and the tripeptide is isolated by column chromatography over Polopak Q or on a thin layer of silica, according to the methods described by Malfroy et al (B. Malfroy, J. P. Swerts, C. Llorens and J. C. Schwartz, Neuro-Science Letters, 11, 329, 1979).

The results obtained with either method have always been consistent.

Determination of the radioactivity of the tripeptide is effected by liquid scintillation spectrometry.

The effect of the inhibitors is established by experiments with increasing concentrations of such materials, which leads to the determination of the 50% inhibitory concentrations calculated by means of data according to the method of Parker and Waud (J. Pharmacol. Exper. Ther. 177, 1, 1971). In some cases, the competitive nature of the inhibition was established by incubation experiments with a fixed concentration of the inhibitor and increasing concentrations of the substrate.

| Derivative No. | 50% inhibitory concentration |
| --- | --- |
| 2 | $7 \times 10^{-8}$ M |
| 4 | $1 \times 10^{-7}$ M |
| 28 | $8 \times 10^{-9}$ M |
| 30 | $1 \times 10^{-7}$ M |
| 38 | $3 \times 10^{-9}$ M |
| 40 | $5 \times 10^{-9}$ M |
| 47 | $3 \times 10^{-9}$ M |
| 63 | $5 \times 10^{-8}$ M |
| 69 | $7 \times 10^{-9}$ M |
| 71 | $2 \times 10^{-7}$ M |
| 99 | $3 \times 10^{-9}$ M |

(II) Protection of the endogenic enkephalinases liberated by depolarisation of the brain sections.

Stratium sections of the rat are incubated in a medium of Krebs-Ringer and the (Met$^5$) enkephalin liberated by addition of 50 mM KCl is evaluated by radioimmunologic dosage (Patey and Coll., Science, 1981, 212, 1153–1155). In the presence of thiorpan, an enkephalinase inhibitor, there is observed an increased recovery of the pentapeptide, which is approximately doubled.

In the presence of a plurality of the compounds according to the present invention, a significantly higher recovery is observed relative to that observed under the effect of thiorphan, even when the latter is present in supramaximal concentration. The higher protection of the liberated enkephalins afforded by these compounds is thence attributed to the inhibition of peptidases (probably aminopeptidases) other than those which are sensitive to thiorphan.

TABLE I

Protection of the liberated endogenic enkephalins by depolarization of strium sections of the rat

| Added inhibitor | | (Met$^5$) liberated enkephalin (pmole/g/min.) |
| --- | --- | --- |
| None | | 120 ± 25 |
| Thiorphan | ($10^{-7}$M) | 280 ± 30* |
| Derivative No. 28 | ($10^{-6}$M) | 550 ± 40* |
| Derivative No. 38 | ($10^{-7}$M) | 600 ± 30* |
| Derivative No. 47 | ($10^{-7}$M) | 630 ± 50* |
| Derivative No. 99 | ($10^{-7}$M) | 600 ± 25* |

*p < 0.001

Thiorphan = HS—CH$_2$—CH—CONH—CH$_2$—CO$_2$H
           |
           CH$_2$—φ

B-Pharmacological studies

The pharmacological study of the products described above showed a specific antalgic, antidiarrhea, antidepressive and hypotensive effect and a potentiation action of the effects of an enkephalin, D Ala$_2$Met Enkephalin (in particular antalgic and hypotensive).

The following pharmacological tests were conducted:

I-Acute toxicity

The determination of the death rate in the mouse is observed after a single intravenous administration of increasing doses of the test compounds.

For all the compounds tested, the LD$_{50}$ is in excess of 100 mg/kg/i.v. and 400 mg/kg by the intraperitoneal route.

II-Subacute toxicity

The derivative 63 was administered by the intraperitoneal route for three weeks to mice at the dose of 50 mg/kg three times a day (150 mg/kg/day). The animals did not exhibit any change in the weight increase rate or any sign of toxicity with respect to the controls. The weight of the organs and their anatomic-pathologic examination after sacrificing the animals showed no difference with respect to the solvent controls.

Further, in the animals in which a reversability test was conducted upon termination of the treatment, no sign of tolerance or habit forming and no weaning phenomena were observed.

III-Antalgic activity (1) Hot plate test

Licking reflex of mice on a plate heated at 55° C. according to the method of Jacob et co-workers (Arch. Int. Pharmacodyn. 122, 287–300, 1959: 133, 296–300, 1961).

(a) Potentiation of the antalgic effect of D Ala$_2$Met Enkephalin:

(α) By the intraventricular route (ivt)

The table I shows that the effect of a subactive dosage (0.3γ) of D Ala$_4$Met Enkephalin when administered by the intraventricular route is significantly potentiated (p<0.05) by the derivatives 28 and 38 at the dose of 30γ and that this effect is antagonised by Naloxone.

(β) By the intravenous route

When administered by the intravenous route, the derivatives No. 2, 30 and 63 at the dose of 30 mg/kg produce a 100% increase in the licking time with respect to animals treated with D Ala$_2$Met Enkephalin (0.3γ intraventricular).

TABLE I

Hot plate Potentiation of the antalgic effect of D Ala$_2$Met Enkephalin and Naxolone-induced antagonism

| Derivative | Dose γ/ mouse ivt | No of mice | % increase in the licking time with respect to animals treated with D Ala$_2$Met enkephalin[1] |
| --- | --- | --- | --- |
| n° 28 + DAla$_2$Met Enkephalin[1] | 30 | 6 | 350* |
| n° 38 + DAla$_2$Met Enkephalin[1] | 30 | 6 | 320* |
| n° 28 + DAla$_2$Met Enkephalin[1] + Naloxone (10 mg/kg ss. cut.) | 30 | 10 | 18 |
| n° 47 | 30 | 10 | 300* |
| n° 99 | 30 | 10 | 280* |

[1] the dose of D Ala$_2$Met Enkephalin is 0.3 γ/mouse, which dose is inactive in itself
*P < 0.05 Wilcoxon's level test (b) Specific antalgic effect By the intravenous route.

The following Table shows that the derivatives No. 2, 30 and 63 have an antalgic effect in the hot plate test (55° C.).

| Derivative | ED$_{50}$ mg/KG/i.v. |
| --- | --- |
| 2 | 30 |
| 30 | 18 |
| 63 | 3 |
| 47 | 25 |
| 99 | 30 |

(2) Test in mice of the withdrawal of the tail immersed in water heated to 48° C. according to the method of Sewell and Spencer (Neuropharmacology, 1976, 15, p. 683–688).

The derivatives 2 and 30 administered by the intravenous route at the dose of 30 mg/kg potentiate very significantly the D Ala$_2$Met Enkephalin administered 15 minutes later by the intraventricular route, at varying subactive doses of from 10 to 30γ/mouse.

This effect is durable and exceeds 2 hours; it is also observed at the dose of 5 mg/kg with the derivative No. 63.

(3) Phenylbenzoquinone or "writhing" test according to the method of Siegmund and co-workers (Proc. Soc. Expert Biol. Med. 1957, 95, 729–731).

The derivatives 2, 30 and 63 injected respectively at the dose of 15, 18 and 1 mg/kg i.v., protect the treated animals from phenylbenzoquinone-induced pain with a significant difference with respect to the controls $p<0.01$. This effect is antagonized by Naloxone.

Here again, if the antinociceptive effects of these compounds are compared with those of Thiorphan, a selective enkephalinase-inhibitor, a distinctly greater maximum effect is observed. For example, thiorphan, even at a heavy dose, never completely eliminates the abdominal stretchings of the mouse, whereas a complete elimination thereof is observed in the case of these compounds. This more pronounced analgesic effect is attributable to an improved protection of the endogenic opioid peptides, in relation with the inhibition not only of the enkephalinase, but also of the aminopeptidases involved in their hydrolysis.

IV-Antidepressive activity

Forced swimming or "Mice Despair" test according to Porsolt's method.

This test is representative of an antidepressive effect.

At the dose of 1 mg/kg i.v., the derivative No. 63 significantly reduces ($p<0.001$) the duration (in seconds) of the immobile periods with respect to the controls.

V-Antidiarrhea activity

It was studied according to the method of Niemegeers and co-workers (Arzneim, Forsh 22, 516, 1972) in which the diarrhea is produced in the rat by means of castor oil.

This effect was moreover found in respect of the doses of 10–30 mg/kg and is antagonized by Naloxone.

VI-Hypotensive activity specific
enkephalin-potentiating activity,
(Laubie M Schmith H., Vincent M., Remon D. Central cardiovascular effects of Morphinometic peptides in dogs. European Journal of Pharmacology, vol. 46, 67–71, 1977).

By the intravenous route, the derivative No. 63 resulted in a reduction in the blood pressure at the dose of 10 mg/kg.

The results of these studies demonstrate the low toxicity and the interesting enkephalinase-inhibiting, antalgic, antidepressive, antidiarrhea and hypotensive properties of the derivatives of the invention which make them applicable in human and veterinary medicine.

The pharmaceutical composition of the invention may be administered to humans by the oral, parenteral or rectal route.

Each unit dose advantageously contains 0.5 to 100 mg of active ingredient. The daily doses administrable may vary from 0.5 mg to 1200 mg of active ingredient.

Having now described our invention what we claim as new and desire to secure by Letters Patent is:

1.

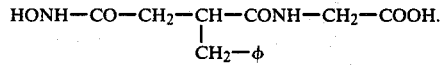

* * * * *